US007411066B2

(12) United States Patent
Hultgren et al.

(10) Patent No.: US 7,411,066 B2
(45) Date of Patent: Aug. 12, 2008

(54) AMINO METHYLATED 2-PYRIDINONES

(75) Inventors: Scott J. Hultgren, St. Louis, MO (US);
Jerome S. Pinkner, St. Louis, MO (US);
Fredrik Almqvist, Umea (SE); Nils Pemberton, Umea (SE); Veronica Aberg, Umea (SE); Andreas Larsson, Umea (SE)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 11/581,518

(22) Filed: Oct. 16, 2006

(65) Prior Publication Data

US 2007/0082887 A1 Apr. 12, 2007

Related U.S. Application Data

(63) Continuation-in-part of application No. PCT/US2005/013032, filed on Apr. 14, 2005.

(60) Provisional application No. 60/563,082, filed on Apr. 16, 2004.

(51) Int. Cl.
*C07D 279/00* (2006.01)
*C07F 9/00* (2006.01)

(52) U.S. Cl. .................... 546/114; 514/301; 514/302

(58) Field of Classification Search ................ 546/116, 546/114
See application file for complete search history.

(56) References Cited

U.S. PATENT DOCUMENTS

| 5,310,562 | A | 5/1994 | Margolin |
| 5,624,677 | A | 4/1997 | El-Rashidy et al. |
| 6,495,539 | B1 | 12/2002 | Hultgren et al. |
| 6,841,559 | B1 * | 1/2005 | Almqvist et al. ............ 514/301 |

FOREIGN PATENT DOCUMENTS

| DE | 84850 | 10/1971 |
| EP | 0133038 A2 | 2/1985 |

OTHER PUBLICATIONS

Svensson et al., Journal of Combinatorial Chemistry, 2000, 2(6), 736-748.*
Pemberton et al. Journal of Organic Chemistry 2004, 69(23), 7830-7835.*
Aggarwal, "Catalytic Asymmetric Synthesis of Epoxides from Aldehydes Using Sulfur Ylides with In Situ Generation of Diazocompounds," 2001, Angew Chem Int Ed, 40/8, pp. 1430-1433.
Alterman, "Fast Microwave-Assisted Preparation of Aryl and Vinyl Nitriles and the Corresponding Tetrazoles from Organo-halides," 2000, J Org Chem, 65, pp. 7984-7989.
Agnew, "Modern Variants of the Mannich Reaction," 1998, Angew Chem Inc, 37, pp. 1044-1070.
Arvela, "Rapid Cyanation of Aryl Iodides in Water Using Microwave Promotion," 2003, Org Biomol Chem, 1, pp. 1119-1121.
Arvela, "Rapid Easy Cyanation of Aryl Bromides and Chlorides Using Nickel Salts in Conjunction with Microwave Promotion," 2003, J Org Chem, 68, pp. 9122-9125.
Asherson, "A General and Practicable Synthesis of Polycyclic Heteroaromatic Compounds. Part 1. Use of a Putative Quinolone-quinone-methide in the Synthesis of Polycyclic Heteroaromatic Compounds," 1980, J Chem Soc Perkin Trans 1, pp. 512-521.
Asherson, "A General and Practicable Synthesis of Polycyclic Heteroaromatic Compounds. Part 2. Reaction of Quinone-methides of Pyrodones, Pyrimidines, Coumarin, and Benzene with Aromatic Amines in a Novel Synthesis of Polycyclic Heteroaromatic Compounds," 1980, J Chem Soc Perkin Trans 1, pp. 522-528.
Bohme, 1976, Advanced Organic Chemistry, 9, p. 107.
Bohme, "Uber die Spaltung von Aminalen und a-Dialkylamino-athern mit Carbonsaurehalogeniden," 1960, Chemische Berichte, 93, pp. 1305-1309. No English translation available.
Brana, "Reaction of N-(2-Pyridylmethyl)-3,5-dimethylbenzamide and N-(3-Pyridylmethyl)-3,5-dimethylbenzamide N-Oxides with Acetic Anhydride," 1982, J Hetero Chem, pp. 1297-1300.
Brown, "Selective Reductions. 29. A Simple Technique to Achieve an Enhanced Rate of Reduction of Representative Organic Compounds by Boran-Dimethyl Sulfide," 1982, J Org Chem, 47, pp.3153-3163.
Brown, "Molecular Addition Compounds. 11. N-Ethyl-N-Isopropylaniline-Borane, A Superior Reagent for Hydroborations and Reductions," 1998, J Org Chem, 63, 5154-5163.
Brown, "Molecular Addition Compounds. 14. Convenient Preparations of Representative Dialkylborane Reagents Using the New, Highly Reactive N-Ethyl-N-Isopropylaniline-Borane Reagent (BACH-EI™)," 1999, Tetrahedron, 55, pp. 5991-6000.
Butler, "4.13 Tetrazoles," 1984, Comprehensive Heterocyclic Chemistry, 5, pp. 791-838, Katritzky and Rees, Eds., Pergamon Press, Oxford.
Cha, "Reaction of Aluminum Hydride-Triethylamine Complex with Selected Organic Compounds Containing Representative Functional Groups," 1993, J Org Chem, 58, pp. 3974-3979.
Clive, "Synthesis of Racemic Brevioxime and Related Model Compounds," 2000, J Org Chem, 65, pp. 4923-4929.
Cox, "Synthesis of Isotopically Labelled 3-Amino-2-Phenylpropionic Acid and Its Role as a Precusor in the Biosynthesis of Tenellin and Tropic Acid," 1991, J Chem Soc Perkin Trans 1, pp. 2537-2540.
Ellis, "Cyanation of Aromatic Halides," 1987, Chem Rev, 87, pp. 779-794.
Emtenas, "An Enantioselective Ketene-Imine Cycloaddition Method for Synthesis of Substituted Ring-Fused 2-Pyridinones," 2001, J Comb Chem, 66, pp. 6756-6761.
Emtenas, "Design and Parallel Solid-Phase Synthesis of Ring-Fused 2-Pyridinones that Target Pilus Biogenesis in Pathogenic Bactera," 2002, J Comb Chem, 4, pp. 630-639.

(Continued)

*Primary Examiner*—D. Margaret Seaman
*Assistant Examiner*—Nizal S Chandrakumar
(74) *Attorney, Agent, or Firm*—Senniger Powers LLP

(57) ABSTRACT

Novel amino methylated 2-pyridinones, precursors, intermediates, and derivatives; the methods for the preparation of the same; uses of the same for inhibiting pili formation in bacteria; and pharmaceutical compositions comprising these compounds are described in this application. The present compounds may be employed to inhibit biofilm formation and thereby inhibit adherence of bacteria to a host cell.

21 Claims, No Drawings

OTHER PUBLICATIONS

Emtenas, "Efficient Mircowave Assisted Synthesis of Optically Active Bicyclic 2-Pyridinones via Δ2-thiazolines," 2003, Molecular Diversity, 7, pp. 165-169.

Hanessian, "Design and Synthesis of Conformationally Constrained Amino Acids as Versatile Scaffolds and Peptide Mimetics," 1997, Tetrahedron, 53(38), pp. 12789-12854.

Hasvold, "Pyridone-Containing Farnesyltransferase Inhibitors: Synthesis and Biological Evaluation," 2003, Bioorganic Med Chem Letters, 13, pp. 4001-4005.

Heaney, "The Generation of Iminium Ions Using Chlorosilanes and their Reactons with Electron Rich Aromatic Heterocycles," 1997, Tetrahedron 53(8), pp. 2941-2958

Jin, "Palladium-Catalyzed Cyanation Reactions of Aryl Chlorides," 2000, Tetrahedron Letters, pp. 3271-3273.

Khanapure, "Intramolecular Sulfur-Assisted NaBH4 Reduction of Esters Synthesis of 5-oxo-ETE and 5-oxo-12-HETE," 2000, Tetrahedron Letterers, 41, 5653-5657

Lange, "A New Mild Method for the Synthesis of Amidines," 1999, Tetrahedron Letters 40, pp. 7067-7070.

Leadbeater, "Ionic Liquids as Reagents and Solvents in Conjunction with Microwave Heating: Rapid Synthesis of Alkyl Halides from Alcohols and Nitriles from Aryl Halides," 2003, Tetrahedron, 59, pp. 2253-2258.

Lee, "Targeting Virulence for Antimicrobial Chemotherapy," 2003, Curr Opin in Pharm, 3, pp. 513-519.

Letinois, "Heterogeneous Rhodium-Catalyzed Hydrogenation Conditions for the Highly Effective Synthesis of 1,3-Oxazolidines from 1,2-Amino Alcohols and Nitriles," 1998, Tetrahedron Letters, 39, pp. 2327-2330.

Li, "The 2-Pyridone Antibacterial Agents: Bacterial Topoisomerase Inhibitors," 2000, Med Res Rev, 20, pp. 231-293.

Mannich, "Ueber ein Kondensationprodukt aus Formaldehyd, Ammoniak und Antipyrin," 1912, W. Arch. Pharm, pp. 647-667 German Text Only Available.

Marlett, "Dimethylethylamine-Alane and N-Methylpyrrolidine-Alane. A Convenient Synthesis of Alane, A Useful Selective Reducing Agent in Organic Synthesis," 1990, J Org Chem, 55, pp. 2968-2969.

Mojtahedi, "Microwave-Assisted Aminomethylation of Electron-Rich Compounds Under Solvent-Free Condition," 2000, Synthetic Comm, 30(1), pp. 69-72.

Mulvey, "Adhesion and Entry of Uropathogenic *Escherichia coli*," 2002, Cell Microbiol, 4(5), pp. 257-271.

Nagarajan, "Design, Synthesis, and Biological Evaluation of Indenoisoquinoline Topoisomerase I Inhibitors Featuring Polyamine Side Chains on the Lactam Nitrogen," 2003, J Med Chem, 46, pp. 5712-5724.

Padwa, "An Isomunchnone-Based Method for the Synthesis of Highly Substituted 2(1H)-Pyridones," 1999, J Org Chem, 64, pp. 8648-8659.

Patel, "Synthesis of Some 6-Substituted Aminopyridin-2(H)-ones & Their Derivatives," 1987 Indian J of Chem, 26B, pp. 1099-1101.

Patrick, "Class I Broad-Spectruc Antibiotics—Ampicillin and Amoxycillin (Beechams 1964)," , 2001, An Introduction to Medicinal Chemistry, 2nd Ed, pp. 400-402, Oxford University Press.

Rounds, "Hydrolysis in the Absence of Bulk Water 2. Chemoselective Hydrolysis of Nitriles Using Tetrahalophthalic Acids," 1988, Tetrahedron Letters, 29(50), pp. 6557-6560.

Sharifi, "Solvent-Free Aminoaklylation of Phenols and Indoles Assisted by Microwave Irradiation," 2001, Monatshefte fur Chemie, 132, pp. 875-880.

Sundermeier, "Palladium-Catalyzed Cyanation of Aryl Halides: Recent Developments sand perspectives," 2003, Eur J Inorg Chem, pp. 3513-3526.

Svensson, "Design and Evaluation of Pilicides: Potential Novel Antibacterial Agents Directed Against Uropathogenic *Escherichia coli*," 2001 Chembiochem, 12, 915-918.

Svensson, "Preparation of Fluorinated Linkers: Use of 19F NMR Spectroscopy to Establish Conditions for Solid-Phase Synthesis of Pilicide Libraries," 2000, J Comb Chem, 2, pp. 736-748.

Thorsett, "Therapeutic Approaches to Alzheimer's Disease," 2000, Curr Opin Chem Biol, 4, pp. 377-382.

Almqvist et al. "Alternative Way of Synthesizing Thiazoline Derivatives" Tetrahedron Letter, 29:2293-2294 (1998).

Barker et al. "3:6-Disubstituted fluorenes. Part II. The preparation of 3:6-diaminofluorene from fluorene, and the attempted internuclear cyclisation of derivatives of 4:4-diaminodiphenylmethane" J. Chem. Soc., pp. 870-873 (1954).

Capps et al. "Synthesis of Bicyclic Pyridone and Dihydropyridone Analogues of B-Lactam Antiobiotics" J. Chem. Soc., Perkin Trans., pp. 3077-3086 (1991).

Casinovi et al. "A New Antibiotic Produced by Strain of *Aspergillus flavipes*" Tetrahedron Letters, 27:3175-3178 (1968).

Fang et al. "Total synthesis of the angiotensin-converting enzyme inhibitor A58365A: On the use of pyroglutamate as a chiral educt" Tetrahedron Letters, 30(28):3621-3624 (1989).

Groutas et al. "Substituted 2-Pyrones, 2-Pyridones, and Other Congeners of Elasnin as Potential Agents for the Treatment of Chronic Obstructive Lung Diseases" J. Med. Chem., 28:1106 (1985).

Head et al. "Validate: A New Method for the Receptor Based Prediction of Binding Affinities of Novel Ligands" J. American Chemical Society, 118:3959-3969 (1996).

Karlsson et al. "Binding Peptides in Solution by the *Escherichia coli* Chaperone PapD as Revealed Using an Inhibition ELISA and NMR Spectroscopy" 6:2085-2101 (1998).

Kuehn et al. "Structural Basis of Pilus Subunit Recotnition by the PapD Chaperone" Science, 262:1234-1241 (1993).

Linn et al. "Solid Phase Synthesis of 1,3,5-Trisubstituted Pyridin-2-ones" Tetrahedron Letters, 40:2227-2230 (1999).

Meyers et al. "Oxazolines XXIV: Chrial Oxazolines and Thiazolines from L-Serine and L-Cysteine. Their Potential Use in Asymetric Synthesis" Heterocycles, 4:1687-1692 (1976).

Mukaiyama et al. "Aromatic Iodination with iodine monochloride by using a catalytic amount of ferrocenium tetrakis (3,5-bis(trifluoromethyl)phenyl) borate" Tetrahedron Letters, 41(49):9383-9386 (2000).

Olthoff et al. "Thiazolo [e,2-a] pyridones" Chemical Abstracts, Abstract No. 72121y, 78(11):474 (1973).

Reidlinger et al. "Synthesen mit Nitrilen, LXXXVII; Cyan-Nitropropenide-Synthone zur Herstellung von Nitropyridinen" Synthesis pp. 835-838 (1991).

W. C. Shakespere "Palladium-Catalyzed Coupling of Lactams with Bromobenzenes" 40:2034-2038 (1999).

Soto et al. "Periplasmic chaperone recognition motiff of subunits mediates quaternery interactions in the pilus" EMBO Journal, 17(21):6155-6167 (1998).

Striker et al. "Structural requirements for the glycolipid receptor of human uropathogenic *Escherichia coli*" Mol. Microbiol. 16:1021-1029 (1995).

Todd et al. "The synthesis of analogs of penicillin I." 75:1895-2000 (1953).

Wittenberger et al. "Dialkyltin Oxide Mediated Addition of Trimethylsilyl Azide to Nitriles. A Novel Preparation of 5-Substituted Tetrazoles" J. Org. Chem., 58:4139-4141 (1998).

Yamamoto et al. "1,3-Oxazines and Related Compounds. XIII. Reaction of Acyl Meldrum's Acids with Schiff Bases Giving 2,3-Disubstituted 5-Acyl-3,4,5,6-tetrahydro-2H-1,3-oxazine-4,6-diones and 2,3,6-Trisubstituted 2,3,-dihydro-1,3-oxazin-4-ones" Chem. Pharm. Bull, 35(5):1860-1870 (1987).

Zhang et al. "Cyclogutenedione-Based Method for the Synthesis of Substituted 2-Pyridinones and Dihydro-2-pyridinones" J. Org. Chem., 64:4042-4049 (1999).

Zhu et al. "The Direct Formation of Unctionalized Alkyl(aryl)zinc Halldes by Oxidative Addition of Highly Reactive Zinc with Organic Halides and their Reactions with Acid Chlorides, a,B-Unsaturated Ketones, and Allylic, Aryl, and Vinyl Halides" J. Org. Chem., 56:1445-1453 (1991).

* cited by examiner

AMINO METHYLATED 2-PYRIDINONES

CROSS REFERENCE TO RELATED APPLICATIONS

This application claims the benefit of U.S. Provisional Application Ser. No. 60/563,082, filed Apr. 16, 2004, and International Patent Application Serial No. PCT/US2005/013032, filed Apr. 14, 2005, the entire content of each of which is hereby incorporated herein by reference.

STATEMENT OF GOVERNMENT RIGHTS

This invention was made with Government support under grant number R37AI295419 awarded by the National Institutes of Health. The Government has certain rights in the invention.

BACKGROUND OF THE INVENTION

The present invention is directed to secondary and tertiary amino methylated 2-pyridinones, to methods of their preparation and to their use for inhibiting pili formation in bacteria.

The core structure of 2-pyridinones, or more commonly referred to as 2-pyridones, is present in a wide range of compounds with diverse biological application areas. Besides showing e.g., antibacterial,[1] antifungal[2] and anti-tumor activity,[3,4] members of these heterocycles also act as inhibitors of a Aβ-peptide aggregation thought to play an important role in Alzheimers' disease.[5] An enantioselective ketene imine cycloaddition reaction to synthesize ring fused substituted 2-pyridones has previously been reported.[6,7] Starting from commercially available nitriles and carboxylic acids, this synthetic pathway rendered a first generation of 2-pyridones that were designed to target periplasmic escort proteins, chaperones, in uropathogenic *Escherichia coli*. Chaperones are essential for the assembly of adhesive protein organelles known as pili or fimbriae present on the surface of the bacteria, in absence of these organelles the bacteria become non-infectious.[8] Thus, compounds interfering with pili/fimbriae formation, pilicides, would represent a novel class of antibacterial agents directed against bacterial virulence considered a promising avenue in drug development.[9]

Encouraging affinity predictions of substituted 2-pyridones binding to the chaperones PapD and FimC have previously been confirmed in vitro by direct binding assays using both surface plasmon resonance techniques and NMR spectroscopy, where the corresponding acid of 4a was found to be a potent binder.[10] Recently, efficient improvements of the original synthetic procedure were reported.[11] This alternative microwave assisted method allows simple and fast preparation of highly substituted 2-pyridones in good yields and with limited racemization. Still, position six is available for further substitution and thus provides an opportunity to introduce hydrophilic functionalities targeting increased bioavailability and enhanced chaperone affinity in the pilicide project. Incorporation of a cyano group would provide a precursor to a number of interesting derivatives such as carboxylic acids,[12] tetrazoles,[13] and amidines.[14] Nitriles can also be converted into primary amines and inspired by former observations in drug development this appeared to be an attractive target. For example in the case of Ampicillin and Amoxycillin, the introduction of an amine substituent led to a broad spectrum antibiotic also affecting Gram-negatives.[15] In addition, introducing amine substituents in the 2-pyridone framework would result in highly substituted rigid amino acids, which could serve as versatile scaffolds and peptide mimetics.[16]

Aromatic cyanodehalogenation and subsequent reduction of the cyano functionality was considered a well cited and straightforward pathway towards amino methylated 2-pyridones.[17,18] As a complement to the primary amines, and to expand the chemical diversity of these structures, tertiary amines were also desired. A few scattered examples where 2-pyridones react with imines in a Mannich reaction in the corresponding position have previously been described[19,20] and recently, microwave mediated Mannich reactions performed with electron-rich aromatic substrates have also been published.[21,22] Nevertheless, applications on more complex structures such as functionalized 2-pyridones with a challenging substitution pattern have previously not been reported.

SUMMARY OF THE INVENTION

Among the various aspects of the present invention are secondary and tertiary amino methylated 2-pyridinones (and their corresponding salts), methods of their preparation and their use for inhibiting pili formation in bacteria.

Briefly, therefore, the present invention is directed to an amino methylated 2-pyridinone corresponding to Formula I or a salt thereof:

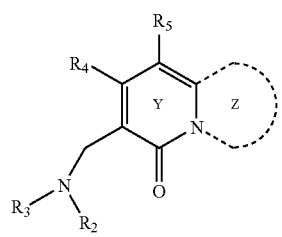

Formula I wherein:

$R_2$ and $R_3$ are independently hydrogen, hydrocarbyl, substituted hydrocarbyl, heterocyclo, or in combination with the nitrogen atom to which they are bonded, form a heterocyclo, provided at least one of $R_2$ and $R_3$ is other than hydrogen;

$R_4$ and $R_5$ are independently hydrogen, hydrocarbyl, substituted hydrocarbyl, or heterocyclo, provided at least one of $R_4$ and $R_5$ is other than hydrogen; and the "Z" ring contains 5 to 7 ring atoms selected from the group consisting of carbon, oxygen, nitrogen and sulfur, provided (i) at least 4 of the ring atoms are carbon when the "Z" ring contains 7 ring atoms, and (ii) at least 3 of the ring atoms are carbon when the "Z" ring contains 5 or 6 ring atoms.

The present invention is further directed to an amino methylated 2-pyridinone corresponding to Formula II or a salt thereof:

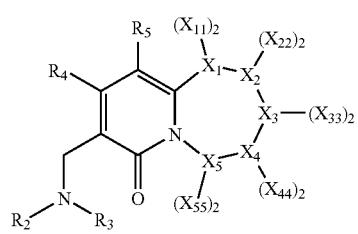

Formula II wherein:

$R_2$ and $R_3$ are independently hydrogen, hydrocarbyl, substituted hydrocarbyl, heterocyclo, or in combination with the nitrogen atom to which they are bonded, form a heterocyclo provided at least one of $R_2$ and $R_3$ is other than hydrogen;

$R_4$ and $R_5$ are independently hydrogen, hydrocarbyl, substituted hydrocarbyl, or heterocyclo, provided at least one of $R_4$ and $R_5$ is other than hydrogen;

$X_1$ is a bond, carbon, oxygen, nitrogen, or sulfur;

$X_2$ is a bond, carbon, oxygen, nitrogen, or sulfur;

$X_3$ and $X_4$ are independently carbon, oxygen, nitrogen, or sulfur;

$X_5$ is carbon or nitrogen;

each $X_{11}$, when present, is an electron pair, hydrogen, hydrocarbyl, substituted hydrocarbyl, heterocyclo, or oxo;

each $X_{22}$, when present, is an electron pair, hydrogen, hydrocarbyl, substituted hydrocarbyl, heterocyclo, or oxo;

each $X_{33}$ and $X_{44}$ is independently an electron pair, hydrogen, hydrocarbyl, substituted hydrocarbyl, heterocyclo, or oxo;

$X_{55}$ is —$CH_2OX_{555}$, —$CH(CO_2X_{555})_2$, —$CH_2CO_2X_{555}$, —$CO_2X_{555}$, —CHO, —$B(OH)_2$, or —$PO(OH)_2$; and $X_{555}$ is hydrogen or other cation, hydrocarbyl, substituted hydrocarbyl, or heterocyclo;

provided, however, (i) $X_{11}$ or $X_{22}$ is not present when $X_1$, or $X_2$ is a bond; and (ii) $X_1$, $X_2$, $X_3$, and $X_4$ are not oxygen, nitrogen or sulfur when $X_5$ is nitrogen.

The present invention is further directed to a compound having the formula

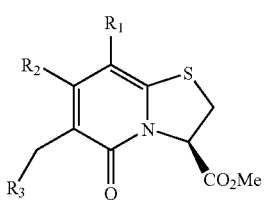

8a-f wherein R1, R2, and R3, in combination, are selected from the combinations identified in the following table as combinations 8a-8f:

| Combination No. | $R^1$ | $R^2$ | $R^3$ |
|---|---|---|---|
| 8a | phenyl | methyl | $NMe_2$ |
| 8b | phenyl | methyl | morpholine |
| 8c | phenyl | $CH_2$-1-naphtyl | $NMe_2$ |
| 8d | phenyl | $CH_2$-1-naphtyl | morpholine |
| 8e | cyclopropyl | $CH_2$-1-naphtyl | $NMe_2$ |
| 8f | cyclopropyl | $CH_2$-1-naphtyl | morpholine |

The present invention is further directed to amino methylated 2-pyridinones corresponding to one or more of Formulae III-VIII (which appear elsewhere herein) or a salt thereof.

The present invention is further directed to a method for the preparation of an amino methylated 2-pyridinone or a salt thereof, the process comprising forming a reaction mixture comprising a 2-pyridinone and an iminium salt, allowing the 2-pyridinone and iminium salt to react to form, via a Mannich reaction, an amino methylated 2-pyridinone corresponding to any of Formulae I-VIII (which appear elsewhere herein), wherein the nitrogen atom of the amino methyl substituent is a tertiary amine.

The present invention is further directed to a method for the preparation of an amino methylated 2-pyridinone or a salt thereof, the process comprising forming a reaction mixture comprising a 2-pyridinone and an iminium salt, allowing the 2-pyridinone and iminium salt to react to form, via a Mannich reaction, an amino methylated 2-pyridinone corresponding to any of Formulae I-VIII (which appear elsewhere herein), wherein the nitrogen atom of the amino methyl substituent is a tertiary amine, and wherein the reaction mixture is irradiated with microwaves.

The present invention is further directed to a method for the preparation of an amino methylated 2-pyridinone or a salt thereof, the process comprising reacting a 2-pyridinone and reducing the formyl substituted 2-pyridinone to form an amino methylated 2-pyridinone corresponding to any of Formulae I-VIII (which appear elsewhere herein), wherein the nitrogen atom of the amino methyl substituent is a secondary amine.

The present invention is further directed to a process for inhibiting adherence of bacteria to a host cell, the process comprising treating the bacteria with a compound of any of Formulae I-VIII (which appear elsewhere herein) or a salt thereof.

The present invention is further directed to a process for inhibiting adherence of bacteria to a host cell, wherein the host cell is in a cell culture and the bacteria is treated by introducing a compound of any of Formula I-VIII (which appear elsewhere herein) or a salt thereof to the cell culture.

Other objects and features of this invention will be in part apparent and in part pointed out hereinafter.

DETAILED DESCRIPTION OF THE INVENTION

In accordance with the present invention, processes have been developed enabling the preparation of secondary and tertiary amino methylated 2-pyridinones. These 2-pyridinones have been found to inhibit or even prevent bacterial infection of host cells by interrupting the formation of pili. Thus, for example, these 2-pyridinones may be employed to inhibit biofilm formation and thereby inhibit adherence of the bacteria to a host cell; this may be accomplished when the composition interferes with the function of chaperones required for the assembly of pili from pilus subunits in diverse Gram-negative bacteria. Such interference is particularly effective since the formation of pili is essential to bacterial pathogenicity and since the production of the pilus subunits in the absence of chaperones is known to be directly toxic.

1. Amino Methylated 2-Pyridinone Compositions

In general, the secondary or tertiary amino methylated 2-pyridinones correspond to Formula 1 or a salt thereof:

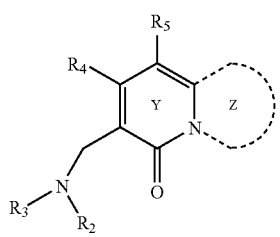

Formula 1 wherein $R_2$ and $R_3$ are independently hydrogen, hydrocarbyl, substituted hydrocarbyl, heterocyclo, or, in combination with the nitrogen atom to which they are bonded, form a heterocyclo, provided at least one of $R_2$ and $R_3$ is other than hydrogen;

$R_4$ and $R_5$ are independently hydrogen, hydrocarbyl, substituted hydrocarbyl, or heterocyclo, provided at least one of $R_4$ and $R_5$ is other than hydrogen; and the "Z" ring contains 5 to 7 ring atoms selected from the group consisting of carbon, oxygen, nitrogen and sulfur, provided (i) at least 4 of the ring atoms are carbon when the "Z" ring contains 7 ring atoms, and (ii) at least 3 of the ring atoms are carbon when the "Z" ring contains 5 or 6 ring atoms.

As previously noted, $R_2$ and $R_3$ are independently hydrogen, hydrocarbyl, substituted hydrocarbyl, heterocyclo, or, in combination with the nitrogen atom to which they are bonded, form a heterocyclo, provided at least one of $R_2$ and $R_3$ is other than hydrogen (i.e., at least one of $R_2$ and $R_3$ is hydrocarbyl, substituted hydrocarbyl or heterocyclo). When one and only one of $R_2$ and $R_3$ is hydrogen, the 2-pyridinone is characterized herein as a secondary amino methylated 2-pyridinone. When neither of $R_2$ and $R_3$ are hydrogen, the 2-pyridinone is characterized herein as a tertiary amino methylated 2-pyridinone.

In one embodiment, the 2-pyridinone is a secondary amino methylated 2-pyridinone and one of $R_2$ and $R_3$ is hydrocarbyl or substituted hydrocarbyl. In this embodiment, for example, $R_2$ or $R_3$ may be alkyl, alkenyl, alkynyl, aryl, or a combination thereof such as alkaryl. In general, when $R_2$ or $R_3$ is alkyl, C1 to C6 alkyls are typically preferred. For example, $R_2$ or $R_3$ may be methyl, ethyl, propyl (straight, branched or cyclic), butyl (straight, branched or cyclic), pentyl, (straight, branched or cyclic), or hexyl (straight, branched or cyclic). Alternatively, $R_2$ or $R_3$ may be substituted alkyl, alkenyl, alkynyl, aryl, or a combination thereof such as substituted alkaryl. For example, $R_2$ or $R_3$ may be substituted methyl, substituted ethyl, substituted propyl (straight, branched or cyclic), substituted butyl (straight, branched or cyclic); substituted pentyl, (straight, branched or cyclic), or substituted hexyl (straight, branched or cyclic) wherein the substituent(s) is/are selected from the group consisting of heterocyclo, alkoxy, alkenoxy, alkynoxy, aryloxy, hydroxy, keto, acyloxy, nitro, amino, amido, thiol, ketal, acetal, ester and ether moieties. In one such embodiment $R_2$ or $R_3$ may be heterocyclo or alkyl.

Alternatively, the 2-pyridinone may be a secondary amino methylated 2-pyridinone and one of $R_2$ and $R_3$ is heterocyclo. In this embodiment, for example, $R_2$ or $R_3$ may be a 5 or 6-membered heterocycle which is saturated, partially unsaturated or fully unsaturated; in addition, the ring atoms of the heterocycle may be further substituted. Exemplary 5 and 6-membered heterocycles include furyl, thienyl, pyridyl, oxazolyl, isoxazolyl, pyrrolyl, indolyl, quinolinyl, and isoquinolinyl. In one embodiment, for example, the heterocycle may be optionally substituted indolyl, furyl, or pyrrolyl. If substituted, the 5 or 6-membered ring may have one or more substituents selected from the group consisting of heterocyclo, alkoxy, alkenoxy, alkynoxy, aryloxy, hydroxy, keto, acyloxy, nitro, amino, amido, thiol, ketal, acetal, ester and ether moieties.

The 2-pyridinone may alternatively be a tertiary amino methylated 2-pyridinone with $R_2$ and $R_3$ independently being selected from hydrocarbyl, substituted hydrocarbyl, and heterocyclo. For example, one of $R_2$ and $R_3$ may be hydrocarbyl or substituted hydrocarbyl when the other of $R_2$ and $R_3$ is heterocyclo. Similarly, one of $R_2$ and $R_3$ may be hydrocarbyl when the other is substituted hydrocarbyl. In each of these embodiments, $R_2$ and $R_3$, the hydrocarbyl, substituted hydrocarbyl, and/or heterocyclo groups may be any of the moieties previously described for $R_2$ or $R_3$ in the embodiment in which the 2-pyridinone is a secondary amino methylated 2-pyridinone. For example, $R_2$ and/or $R_3$ may be alkyl, alkenyl, alkynyl, aryl, or a combination thereof such as alkaryl. In general, when $R_2$ and/or $R_3$ is alkyl, C1 to C6 alkyls are typically preferred. Thus, $R_2$ and/or $R_3$ may be methyl, ethyl, propyl (straight, branched or cyclic), butyl (straight, branched or cyclic), pentyl, (straight, branched or cyclic), or hexyl (straight, branched or cyclic). Alternatively, $R_2$ and/or $R_3$ may be substituted alkyl, alkenyl, alkynyl, aryl, or a combination thereof such as substituted alkaryl. For example, $R_2$ and/or $R_3$ may be substituted methyl, substituted ethyl, substituted propyl (straight, branched or cyclic), substituted butyl (straight, branched or cyclic), substituted pentyl, (straight, branched or cyclic), or substituted hexyl (straight, branched or cyclic) wherein the substituent(s) is/are selected from the group consisting of heterocyclo, alkoxy, alkenoxy, alkynoxy, aryloxy, hydroxy, keto, acyloxy, nitro, amino, amido, thiol, ketal, acetal, ester and ether moieties. By way of further example, $R_2$ and/or $R_3$ may be a 5 or 6-membered heterocycle which is saturated, partially unsaturated or fully unsaturated. Exemplary 5 and 6-membered heterocycles include furyl, thienyl, pyridyl, oxazolyl, isoxazolyl, pyrrolyl, indolyl, quinolinyl, and isoquinolinyl. In one such embodiment, the 5 or 6-membered ring is unsubstituted. In another embodiment, the 5 or 6-membered ring has one or more substituents selected from the group consisting of heterocyclo, alkoxy, alkenoxy, alkynoxy, aryloxy, hydroxy, keto, acyloxy, nitro, amino, amido, thiol, ketal, acetal, ester and ether moieties. In general, when $R_2$ and/or $R_3$ is aryl monocyclic or bicyclic groups containing from 6 to 12 carbons in the ring portion are typically preferred. Thus, $R_2$ and/or $R_3$ may be phenyl, biphenyl, naphthyl, substituted phenyl, substituted biphenyl or substituted naphthyl.

In a further embodiment, the 2-pyridinone is a tertiary amino methylated 2-pyridinone with $R_2$, $R_3$ and the nitrogen atom to which they are each bonded defining a nitrogen-containing heterocyclo. In this embodiment, for example, $R_2$, $R_3$ and the nitrogen atom to which they are each bonded define a 5- or 6-membered nitrogen-containing ring such as substituted morpholine, piperidine, or 2- or 4-pyrolidine. Optionally, the heterocyclo ring is substituted by one or more substituents selected from the group consisting of heterocyclo, alkoxy, alkenoxy, alkynoxy, aryloxy, hydroxy, keto, acyloxy, nitro, amino, amido, thiol, ketal, acetal, ester and ether moieties In a further embodiment of the amino methylated 2-pyridinone, (i) $R_2$ and $R_3$ are independently hydrogen, hydrocarbyl, substituted hydrocarbyl or heterocyclo, provided at least one of $R_2$ and $R_3$ is other than hydrogen and (ii) each $X_{11}$, when present, is an electron pair, hydrogen, hydrocarbyl, substituted hydrocarbyl, heterocyclo, or oxo.

In general, $R_4$ and $R_5$ are independently hydrogen, hydrocarbyl, substituted hydrocarbyl, or heterocyclo, provided at least one of $R_4$ and $R_5$ is other than hydrogen (i.e., at least one of $R_4$ and $R_5$ is hydrocarbyl, substituted hydrocarbyl or heterocyclo). For example, $R_4$ may be hydrocarbyl, substituted hydrocarbyl or heterocyclo when $R_5$ is hydrogen. Alternatively, $R_5$ may be hydrocarbyl, substituted hydrocarbyl or heterocyclo when $R_4$ is hydrogen. In another embodiment, each of $R_4$ and $R_5$ are selected independently from hydrocarbyl, substituted hydrocarbyl and heterocyclo. That is, one of $R_4$ and $R_5$ may be hydrocarbyl or substituted hydrocarbyl when the other of $R_4$ and $R_5$ is heterocyclo. Similarly, one of $R_4$ and $R_5$ may be hydrocarbyl when the other is substituted hydrocarbyl. In each of these embodiments, the hydrocarbyl, substituted hydrocarbyl, and/or heterocyclo groups may be any of the moieties previously described for $R_2$ and $R_3$. In one presently preferred embodiment, each of $R_4$ and $R_5$ is hydrocarbyl. For example, one of $R_4$ and $R_5$ may be aryl (e.g., phenyl or naphthyl) when the other is alkyl. In general, when $R_4$ and/or $R_5$ is alkyl, C3 to C15 alkyls are typically preferred. For example, when $R_4$ and/or $R_5$ is alkyl, one or both substituents may be methyl, ethyl, propyl, isopropyl, butyl, hexyl, octyl, nonyl, undecyl, dodecyl and the like. Alternatively, one of $R_4$ and $R_5$ may be phenyl when the other is naphthyl.

As depicted in Formula 1, the "Z" ring, together with the "Y" ring forms a fused, bicyclic ring system. As depicted, the "Y" ring contains six ring atoms with one of the ring atoms being nitrogen. As previously defined, the "Z" ring contains 5 to 7 ring atoms, with two of these 5 to 7 ring atoms (i.e., one nitrogen and one carbon atom) also being part of the "Y" ring. The remaining atoms of the "Z" ring are selected from the group consisting of carbon, oxygen, nitrogen, and sulfur, provided, however, when the "Z" ring is a 6 or 7-membered ring, no more than three ring atoms of the "Z" ring are oxygen, nitrogen, or sulfur, or a combination thereof and when the "Z" ring is a 5-membered ring, no more than two ring atoms of the "Z" ring are oxygen, nitrogen, or sulfur, or a combination thereof. Stated another way, when the "Z" ring is a 6 or 7-membered ring, in addition to the nitrogen atom which is shared by the X and Y rings, two additional ring atoms in the "Z" ring may be selected from oxygen, nitrogen and sulfur and when the "Z" ring is a 5-membered ring, in addition to the nitrogen atom which is shared by the X and Y rings, one additional ring atom in the "Z" ring may be selected from oxygen, nitrogen and sulfur.

In one such embodiment, the "Z" ring is a 5, 6 or 7-membered saturated or partially unsaturated ring. For example, in this embodiment the compound may correspond to Formula II:

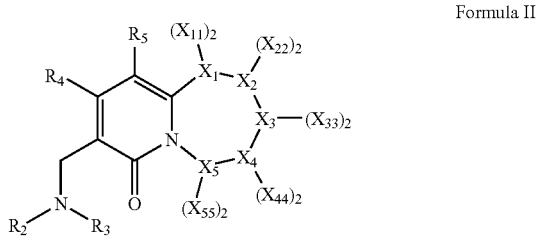

Formula II wherein $R_2$, $R_3$, $R_4$, and $R_5$ are as defined in connection with Formula I and each of the permutations thereof;

$X_1$ is a bond, carbon, oxygen, nitrogen, or sulfur;

$X_2$ is a bond, carbon, oxygen, nitrogen, or sulfur;

$X_3$ and $X_4$ are independently carbon, oxygen, nitrogen, or sulfur;

$X_5$ is carbon or nitrogen;

each $X_{11}$, when present, is an electron pair, hydrogen, hydrocarbyl, substituted hydrocarbyl, heterocyclo, oxo, halo, or acyl;

each $X_{22}$, when present, is an electron pair, hydrogen, hydrocarbyl, substituted hydrocarbyl, heterocyclo, or oxo;

each $X_{33}$ and $X_{44}$ is independently an electron pair, hydrogen, hydrocarbyl, substituted hydrocarbyl, heterocyclo, or oxo;

$X_{55}$ is $—CH_2OX_{555}$, $—CH(CO_2X_{555})_2$, $—CH_2CO_2X_{555}$, $—CO_2X_{555}$, $—CHO$, $—B(OH)_2$, or $—PO(OH)_2$; and $X_{555}$ is hydrogen or other cation, hydrocarbyl, substituted hydrocarbyl, or heterocyclo;

provided, however, (i) $X_{11}$, or $X_{22}$ is not present when $X_1$, or $X_2$, respectively, is a bond; (ii) no more than two of $X_1$, $X_2$, $X_3$, $X_4$ and $X_5$ are oxygen, nitrogen or sulfur when the "Z" ring contains 6 or 7 ring atoms, and (iii) no more than one of $X_1$, $X_2$, $X_3$, $X_4$ and $X_5$ are oxygen, nitrogen or sulfur when the "Z" ring contains 5 ring atoms.

In this embodiment, $R_2$, $R_3$, $R_4$, and $R_5$ may be present in each of the permutations previously described in connection with Formula I. For example, the compound corresponding to Formula II, or salt thereof, may be a secondary amino methylated 2-pyridinone (wherein one, but only one of $R_2$ and $R_3$ is hydrogen); in this embodiment, one of $R_2$ and $R_3$ is hydrocarbyl, substituted hydrocarbyl or heterocyclo with the hydrocarbyl, substituted hydrocarbyl or heterocyclo being as described in connection with Formula I. Alternatively, the compound corresponding to Formula II, or salt thereof, may be a tertiary amino methylated 2-pyridinone (wherein neither $R_2$ or $R_3$ is hydrogen); in this embodiment, each of $R_2$ and $R_3$ are independently hydrocarbyl, substituted hydrocarbyl or heterocyclo with the hydrocarbyl, substituted hydrocarbyl or heterocyclo moieties and each of the possible permutations thereof being as described in connection with Formula I.

As depicted, the "Z" ring, i.e., the ring defined by $X_1$-$X_5$ and the carbon and nitrogen atoms to which $X_1$ and $X_5$, respectively, are bonded, may be a five, six or seven-membered ring. When the "Z" ring is a seven-membered ring, neither $X_1$ nor $X_2$ is a bond. When the "Z" ring is a six-membered ring, however, $X_1$ is a bond directly linking $X_2$ to the carbon atom of the other ring of the fused bicyclic system (i.e., the ring designated as the "Y" ring in Formula I). When the "Z" ring is a five-membered ring, $X_1$ and $X_2$, in combination, define a bond directly linking $X_3$ to the carbon atom of the other ring of the fused bicyclic system (i.e., the ring designated as the "Y" ring in Formula I). When the "Z" ring is a six-membered ring, therefore, neither $X_{11}$ is present since the ring atom to which each $X_{11}$ is shown as being a substituent is not present. Similarly, when the "Z" ring is a five-membered ring, neither of the $X_{11}$ substituents nor either of the $X_{12}$ substituents is present since the ring atoms to which they are shown as being attached are not present.

As depicted in Formula II, $X_1$-$X_5$ are substituted by two $X_{11}$-$X_{55}$ substituents, respectively. As defined, each $X_{11}$-$X_{55}$ may be an electron pair; for example, one or more of $X_{11}$-$X_{55}$ may be an electron pair when two or more of $X_1$-$X_5$ are not fully saturated, e.g., an $Sp^2$ hybridized carbon. Alternatively, one or more of $X_{11}$-$X_{55}$ may be an electron pair when one of $X_1$-$X_5$ is oxygen, sulfur or nitrogen. Thus, for example, one of $X_1$-$X_5$ may be a saturated nitrogen atom bonded to two other ring atoms and a corresponding substituent designated $X_{11}$-$X_{55}$ (depending upon the ring position of nitrogen atom) with the other corresponding substituent designated $X_{11}$-$X_{55}$ being an electron pair of the nitrogen atom. Also, it is contemplated that a sulfur or ring nitrogen atom may be in any of their available oxidation states. For example, a ring sulfur atom may be in sulfide oxidation state (—S—), the sulfoxide oxidation state (—SO—), or the sulfone oxidation state (—$SO_2$—). Similarly, a ring nitrogen atom may be in its N-oxide oxidation state (—N(=O)—). For example, if $X_1$ is sulfur, each $X_{11}$ may be an electron pair (which corresponds to the sulfide oxidation state), one $X_{11}$ may be an electron pair when the other is oxo (which corresponds to sulfoxide oxidation state) or each $X_{11}$ may be oxo (which corresponds to the sulfone oxidation state).

In one embodiment, $X_{55}$ is an acyl or acyl-containing moiety. For example, in this embodiment $X_{55}$ may be —CH$(CO_2X_{555})_2$, —$CH_2CO_2X_{555}$, —$CO_2X_{555}$, or —CHO. In a further embodiment, $X_{55}$ may be —CH$(CO_2X_{555})_2$. In general, $X_{555}$ is preferably hydrogen or another cation such as an alkali metal, an alkaline earth metal or ammonium in this embodiment. In another embodiment, $X_{55}$ may be —CH$(CO_2X_{555})_2$, —CH$_2CO_2X_{555}$, or —CO$_2X_{555}$. In another embodiment, $X_{55}$ may be —CH$(CO_2X_{555})_2$ or —CH$_2CO_2X_{555}$. In still another embodiment, $X_{55}$ may be —CH$(CO_2X_{555})_2$. In a further embodiment, $X_{55}$ is —B(OH)$_2$, —PO(OH)$_2$, or tetrazole.

While the "Z" ring may be seven-membered in one embodiment, it is presently preferred that the "Z" ring be a five or six-membered ring. In this embodiment, the secondary or tertiary amino methylated 2-pyridinone corresponds to Formula III:

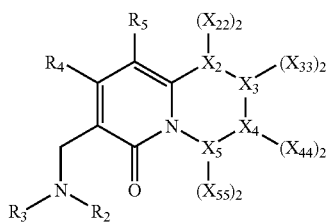

Formula III wherein $R_2$, $R_3$, $R_4$, $R_5$, $X_2$, $X_3$, $X_4$, $X_5$, $X_{22}$, $X_{33}$, $X_{44}$, and $X_{55}$ are as described in connection with Formula II and each of the permutations thereof. In one embodiment, $X_{33}$ and $X_{44}$ is independently an electron pair, hydrogen, hydrocarbyl, substituted hydrocarbyl, heterocyclo, oxo, halo or acyl.

Still more preferably, the "Z" ring is a 5-membered ring. For example, in this embodiment, the secondary or tertiary amino methylated 2-pyridinone compound corresponds to Formula IV:

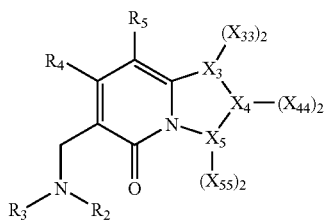

Formula IV wherein $R_2$, $R_3$, $R_4$, $R_5$, $X_3$, 4, $X_5$, $X_{33}$, $X_{44}$, and $X_{55}$ are as described in connection with Formula II and each of the permutations thereof. In one embodiment, each $X_{44}$ is independently an electron pair, hydrogen, hydrocarbyl, substituted hydrocarbyl, heterocyclo, oxo, halo or acyl.

When the secondary or tertiary amino methylated 2-pyridinone compound corresponds to Formula IV and $X_4$ is carbon, a chiral center may exist at the ring position occupied by $X_5$. Thus, for example, isomers corresponding to Formula Va and Vb may exist:

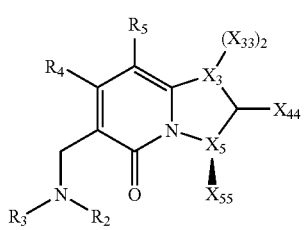

Formula Va

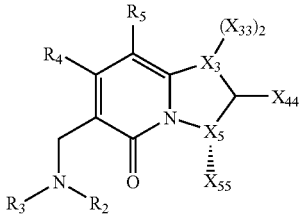

Formula Vb wherein $R_2$, $R_3$, $R_4$, $R_5$, $X_3$, $X_5$, $X_{33}$, $X_{44}$, and $X_{55}$ are as described in connection with Formula II and each of the permutations thereof. In one embodiment, the secondary or tertiary amino methylated 2-pyridinone compound corresponds to Formula Va. In another embodiment, the secondary or tertiary amino methylated 2-pyridinone compound corresponds to Formula Vb. In another embodiment, each $X_{44}$ is hydrogen, hydrocarbyl, halo or acyl.

In one preferred embodiment of the present invention, the "Z" ring is a 5-membered ring containing a sulfur atom. For example, in this embodiment, the compound may correspond to Formula VIa or VIb:

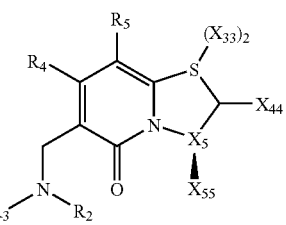

Formula VIa

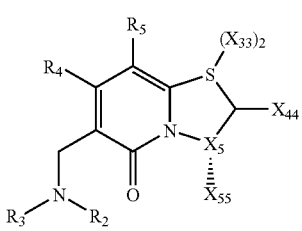

Formula VIb wherein $R_2$, $R_3$, $R_4$, $R_5$, $X_5$, $X_{33}$, $X_{44}$, and $X_{55}$ are as described in connection with Formula II and each of the permutations thereof.

In one embodiment in which the secondary or tertiary amino methylated 2-pyridinone corresponds to Formula VI, sulfur is in the sulfide oxidation state (i.e., each $X_{33}$ is an electron pair). In another such embodiment, sulfur is in the sulfoxide oxidation state (i.e., one $X_{33}$ is an electron pair and the other is oxo (=O)). In yet another such embodiment, sulfur is in the sulfone oxidation state (i.e., each $X_{33}$ is oxo (=O)). In yet another embodiment, $X_{44}$ is hydrogen, hydrocarbyl, substituted hydrocarbyl, heterocyclo, oxo, halo or acyl. In still another embodiment, $X_{44}$ is hydrogen, alkyl, halo, —C(O)R$_{44}$ or —C(O)N(R$_{44}$)$_2$ and each R$_{44}$ is independently hydrogen, alkyl or aryl. In another embodiment, $X_{55}$ is —CO$_2X_{555}$. In yet another embodiment, $X_{555}$ may be hydrogen, alkyl, or an alkaline metal. In still another embodiment, (i) $R_2$ and $R_3$ are independently hydrogen, hydrocarbyl, substituted hydrocarbyl or heterocyclo, and (ii) $X_{44}$ is hydrogen, hydrocarbyl, substituted hydrocarbyl, heterocyclo, or oxo. In yet another embodiment, $R_2$ is alkyl. In anther embodiment, $R_2$ and $R_3$, in combination with the nitrogen atom to which they are bonded from a heterocyclo. In another embodiment, $R_4$ is alkyl or aryl. In another embodiment, $R_5$ is alkyl.

When the secondary or tertiary amino methylated 2-pyridinone corresponds to Formula VI, $X_{44}$ may have any of the values previously described for $X_{44}$. Typically, however, $X_{44}$ will be hydrogen or hydrocarbyl. More typically, $X_{44}$ will be hydrogen.

In one preferred embodiment of the present invention, the "Z" ring is a saturated 5-membered ring. For example, in this embodiment, the compound may correspond to Formula VIIa or VIIb:

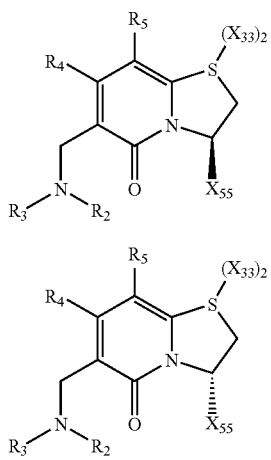

Formula VIIa

Formula VIIb wherein $R_2$, $R_3$, $R_4$, $R_5$, $X_{33}$, and $X_{55}$ are as described in connection with Formula II and each of the permutations thereof.

When the secondary or tertiary amino methylated 2-pyridinone corresponds to Formula VIIa or VIIb, the sulfur atom may be in the sulfide oxidation state (i.e., each $X_{33}$ is an electron pair). Alternatively, the sulfur atom may be in the sulfoxide oxidation state (i.e., one $X_{33}$ is an electron pair and the other is oxo (=O)). The sulfur atom may also be in the sulfone oxidation state (i.e., each $X_{33}$ is oxo (=O)).

In one embodiment, the 2-pyridinone corresponds to Formula VIIa or VIIb, one of $R_2$ and $R_3$ is hydrogen and the other is hydrocarbyl or substituted hydrocarbyl. In this embodiment, for example, one of $R_2$ or $R_3$ is hydrogen and the other is alkyl, alkenyl, alkynyl, aryl, or a combination thereof such as alkaryl. For example, $R_2$ or $R_3$ may be optionally substituted methyl, ethyl, propyl (straight, branched or cyclic), butyl (straight, branched or cyclic), pentyl, (straight, branched or cyclic), or hexyl (straight, branched or cyclic) wherein the substituent(s) is/are selected from the group consisting of heterocyclo, alkoxy, alkenoxy, alkynoxy, aryloxy, hydroxy, keto, acyloxy, nitro, amino, amido, thiol, ketal, acetal, ester and ether moieties. In one such embodiment $R_2$ or $R_3$ may be heterocyclo or alkyl.

Alternatively, the 2-pyridinone may correspond to Formula VIIa or VIIb wherein one of $R_2$ and $R_3$ is hydrogen and the other is heterocyclo. In this embodiment, for example, $R_2$ or $R_3$ may be optionally substituted furyl, thienyl, pyridyl, oxazolyl, isoxazolyl, pyrrolyl, indolyl, quinolinyl, and isoquinolinyl. In one particular embodiment, for example, the heterocycle may be optionally substituted indolyl, furyl, or pyrrolyl. If substituted, the 5 or 6-membered ring may have one or more substituents selected from the group consisting of heterocyclo, alkoxy, alkenoxy, alkynoxy, aryloxy, hydroxy, keto, acyloxy, nitro, amino, amido, thiol, ketal, acetal, ester and ether moieties.

The 2-pyridinone may alternatively correspond to Formula VIIa or VIIb wherein each of $R_2$ and $R_3$ are independently selected from hydrocarbyl, substituted hydrocarbyl, and heterocyclo. For example, one of $R_2$ and $R_3$ may be hydrocarbyl or substituted hydrocarbyl when the other of $R_2$ and $R_3$ is heterocyclo. Similarly, one of $R_2$ and $R_3$ may be hydrocarbyl when the other is substituted hydrocarbyl. In each of these embodiments, the $R_2$ and $R_3$ hydrocarbyl, substituted hydrocarbyl, and/or heterocyclo groups may be any of the moieties previously described for $R_2$ or $R_3$ in connection with Formulae VIIa and VIIb, and the various permutations thereof. For example, $R_2$ and/or $R_3$ may be alkyl, alkenyl, alkynyl, aryl, or a combination thereof such as alkaryl. In general, when $R_2$ and/or $R_3$ is alkyl, C1 to C6 alkyls are typically preferred. Thus, $R_2$ and/or $R_3$ may be methyl, ethyl, propyl (straight, branched or cyclic), butyl (straight, branched or cyclic), pentyl, (straight, branched or cyclic), or hexyl (straight, branched or cyclic). Alternatively, $R_2$ and/or $R_3$ may be substituted alkyl, alkenyl, alkynyl, aryl, or a combination thereof such as substituted alkaryl. For example, $R_2$ and/or $R_3$ may be substituted methyl, substituted ethyl, substituted propyl (straight, branched or cyclic), substituted butyl (straight, branched or cyclic), substituted pentyl, (straight, branched or cyclic), or substituted hexyl (straight, branched or cyclic) wherein the substituent(s) is/are selected from the group consisting of heterocyclo, alkoxy, alkenoxy, alkynoxy, aryloxy, hydroxy, keto, acyloxy, nitro, amino, amido, thiol, ketal, acetal, ester and ether moieties. By way of further example, $R_2$ and/or $R_3$ may be a 5 or 6-membered heterocycle which is saturated, partially unsaturated or fully unsaturated. Exemplary 5 and 6-membered heterocycles include furyl, thienyl, pyridyl, oxazolyl, isoxazolyl, pyrrolyl, indolyl, quinolinyl, and isoquinolinyl, In one such embodiment, the 5 or 6-membered ring is unsubstituted. In another embodiment, the 5 or 6-membered ring has one or more substituents selected from the group consisting of heterocyclo, alkoxy, alkenoxy, alkynoxy, aryloxy, hydroxy, keto, acyloxy, nitro, amino, amido, thiol, ketal, acetal, ester and ether moieties. By way of further example, one of $R_2$ and/or $R_3$ may be optionally substituted aryl when the other is hydrocarbyl, substituted hydrocarbyl or heterocyclo wherein the hydrocarbyl, substituted hydrocarbyl or heterocyclo moieties may be as previously described in connection with $R_2$ and/or $R_3$.

In a further embodiment, the 2-pyridinone is a tertiary amino methylated 2-pyridinone with $R_2$, $R_3$ and the nitrogen atom to which they are each bonded defining a nitrogen-containing heterocyclo. In this embodiment, for example, $R_2$, $R_3$ and the nitrogen atom to which they are each bonded define a 5- or 6-membered nitrogen-containing ring such as morpholino, pyrrolyl, or pipridine. Optionally, the heterocyclo ring is substituted by one or more substituents selected from the group consisting of heterocyclo, alkoxy, alkenoxy, alkynoxy, aryloxy, hydroxy, keto, acyloxy, nitro, amino, amido, thiol, ketal, acetal, ester and ether moieties.

In general, $R_4$ and $R_5$ are independently hydrogen, hydrocarbyl, substituted hydrocarbyl, or heterocyclo, provided at least one of $R_4$ and $R_5$ is other than hydrogen (i.e., at least one of $R_4$ and $R_5$ is hydrocarbyl, substituted hydrocarbyl or heterocyclo). For example, $R_4$ may be hydrocarbyl, substituted hydrocarbyl or heterocyclo when $R_5$ is hydrogen. Alternatively, $R_5$ may be hydrocarbyl, substituted hydrocarbyl or heterocyclo when $R_4$ is hydrogen. In another embodiment, each of $R_4$ and $R_5$ are selected independently from hydrocarbyl, substituted hydrocarbyl and heterocyclo. That is, one of $R_4$ and $R_5$ may be hydrocarbyl or substituted hydrocarbyl when the other of $R_4$ and $R_5$ is heterocyclo. Similarly, one of $R_4$ and $R_5$ may be hydrocarbyl when the other is substituted hydrocarbyl. In each of these embodiments, the hydrocarbyl, substituted hydrocarbyl, and/or heterocyclo groups may be any of the moieties previously described for $R_2$ and $R_3$. In one presently preferred embodiment, each of $R_4$ and $R_5$ is hydrocarbyl. For example, one of $R_4$ and $R_5$ may be aryl (e.g., phenyl or naphthyl) when the other is alkyl. In general, when $R_4$ and/or $R_5$ is alkyl, C3 to C15 alkyls are typically preferred. Alternatively, one of $R_4$ and $R_5$ may be phenyl when the other is naphthyl.

In another preferred embodiment of the present invention, the "Z" ring is a saturated 5-membered ring. For example, in this embodiment, the compound may correspond to Formula VIIIa or VIIIb:

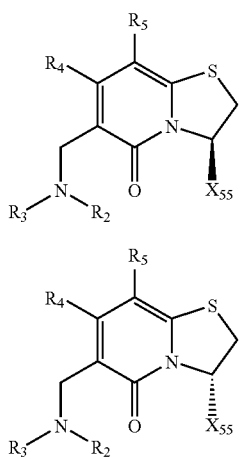

Formula VIIIa

Formula VIIIb wherein $R_2$, $R_3$, $R_4$, $R_5$, and $X_{55}$ are as described in connection with Formula II and each of the permutations thereof.

The compounds corresponding to Formulae I-VIII and the salts thereof may have one or more asymmetric carbons and thus, the compositions may exist in diastereomeric, racemic or optically active forms. All of these stereoisomers are contemplated within the scope of the present invention. More particularly, the present invention includes the enantiomers, diastereomers, racemic mixtures and other mixtures thereof.

The compounds corresponding to Formula I-VIII may be in the form of free bases or pharmaceutically acceptable acid addition salts or other salts thereof. The term "pharmaceutically-acceptable salts" embraces salts commonly used to form alkali metal salts and to form addition salts of free acids or free bases. The nature of the salt may vary, provided that it is pharmaceutically-acceptable. Suitable pharmaceutically-acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, P-hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, for example, the appropriate acid or base with the compound of any Formula set forth herein.

2. Synthetic Processes

In general, tertiary amino methylated 2-pyridinones may be prepared via the Mannich reaction using the corresponding 2-pyridinone and an iminium salt according to the following reaction scheme:

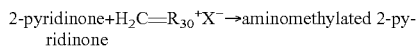

wherein the amino methylated 2-pyridinone corresponds to any of Formulae I-VIII described above, $R_{30}^+$ is a disubstituted quaternary nitrogen atom, $X^-$ is a halide and the 2-pyridinone corresponds to any of Formulae I-VIII described above, except that the 2-pyridinone lacks the aminomethyl substituent. Thus, for example, in one embodiment the tertiary amino methylated 2-pyridinone corresponding to Formula I may be prepared according to the following reaction scheme:

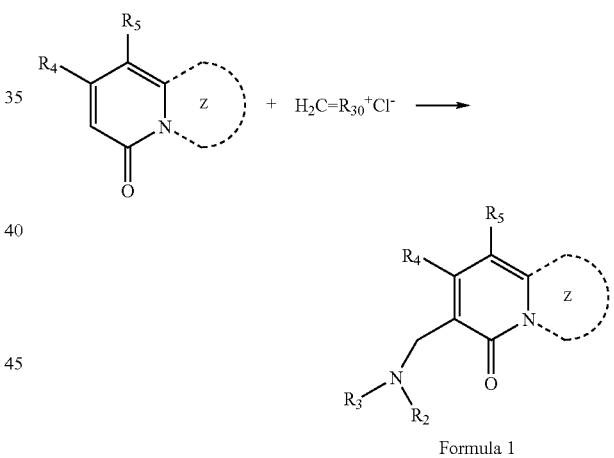

Formula 1 wherein $R_2$, $R_3$, $R_4$, and $R_5$ are as defined in connection with Formula I, $X^-$ is a halide, preferably chloride or iodide, and $R_{30}^+$ is a disubstituted quaternary nitrogen atom with the substituents of the nitrogen atom corresponding to $R_2$ and $R_3$. Alternatively, therefore, the iminium salt may be represented by the formula $H_2C=N(R_2)(R_3)^+X^-$ wherein $X^-$ is a halide, and $R_2$ and $R_3$ are as previously defined. Thus, in one embodiment, $R_2$ and $R_3$ may each be alkyl; for example, $R_2$ and $R_3$ may each be methyl, ethyl and the like. Alternatively, $R_2$ and $R_3$ may, in combination with the ammonium nitrogen atom to which they are attached, define a nitrogen-containing 5 or 6-membered ring such as morpholino, pyrrolyl, or pipridine.

In general, the reaction may be carried out over a range of temperatures and in a range of solvents in which the reactants are soluble. Exemplary solvents include acetonitrile, toluene, N-methyl-2-pyrrolidinone, dimethylformamide, dichloroethane and dichloromethane. Typically, the reaction will be carried out at a temperature in excess of 60° C., preferably at a temperature in excess of 100° C.

To potentially reduce reaction times and/or increase yields, the reaction mixture may be irradiated with microwaves. In general, the microwaves preferably have a wavelength of 1 mm-1 m corresponding and a power of 0.3-300 Ghz. Typically, the microwaves have a wavelength of 12.2 cm and a power of 2.45 Ghz. The reaction mixture may be irradiated for a period from seconds to minutes, with irradiation times typically being in the range of about four minutes to about fourteen minutes. During irradiation, the reaction mixture is preferably maintained at a temperature of about 80° C. to about 180° C., more preferably about 130° C. to about 150° C.

Secondary amino methylated 2-pyridinone may be prepared in a somewhat similar manner, except that a halogenated iminium salt is substituted for the iminium salt in the first reaction step. This produces a formyl substituted pyridinone which can be reductively aminated using a reducing agent and an amine according to the following reaction scheme:

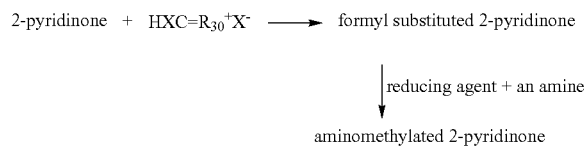

wherein the amino methylated 2-pyridinone corresponds to any of Formulae I-VIII described above, $R_{30}^+$ is a disubstituted quaternary nitrogen atom, X is halogen and the 2-pyridinone corresponds to any of Formulae I-VIII described above, except that the 2-pyridinone lacks the aminomethyl substituent. Thus, for example, in one embodiment the tertiary amino methylated 2-pyridinone corresponding to Formula I may be prepared according to the following reaction scheme:

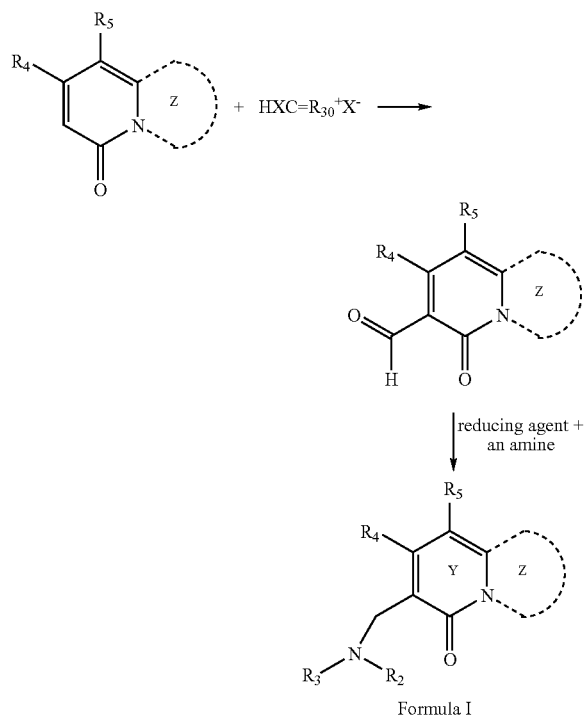

Formula I wherein $R_2$, $R_3$, $R_4$, and $R_5$ are as defined in connection with Formula I, X is halogen, preferably chloride or iodine, $R_{30}^+$ is a quaternary nitrogen atom, and the amine is a secondary amine represented by the formula $NHR_2R_3$, wherein $R_2$ and $R_3$ are as described above. Thus, in one embodiment, $R_2$ and $R_3$ may each be alkyl; for example, $R_2$ and $R_3$ may each be methyl, ethyl and the like. Alternatively, $R_2$ and $R_3$ may, in combination with the ammonium nitrogen atom to which they are attached, define a nitrogen-containing 5 or 6-membered ring such as morpholino, pyrrolyl, or pipridine.

In general, the reducing agent may be any conventional reducing agent, provided the reducing agent does not undesirably reduce other substituents in the molecule. Preferably a nucleophilic reducing agent is used. For example, under appropriate conditions the reducing agent may be $H_2$ gas and an organometalic. In general, borohydrides such as sodium borohydrides or sodium 3-acetoxy borohydride are preferred. Alternatively, a borohydride such as sodium cyanoborohydride may be used.

The reaction may be carried out over a range of temperatures and in a range of solvents in which the reactants are soluble. Exemplary solvents include acetonitrile, toluene, N-methyl-2-pyrrolidinone, dimethylformamide, and dichloroethane. Typically, the reaction will be carried out at a temperature in excess of 0° C., preferably at a temperature in excess of 20° C.

3. Uses

Compounds corresponding to any of Formulae I-VIII and the salts thereof may be used in vitro or in vivo to inhibit pili formation by bacteria. Thus, for example, a compound of the present invention or a salt thereof may be introduced to a cell culture to inhibit pili formation. Alternatively, a compound of the present invention or a salt thereof may be administered to a mammal to inhibit pili formation in vivo. In a further alternative, a prosthetic implant may be coated with a compound of the present invention or salt thereof before the prosthesis is implanted in a patient's body.

For in vivo applications, a pharmaceutical composition comprising an effective amount of a compound of the present invention (or salt thereof) in combination with at least one pharmaceutically or pharmacologically acceptable carrier is administered to an animal, including humans. The carrier, also known in the art as an excipient, vehicle, auxiliary, adjuvant, or diluent, is any substance which is pharmaceutically inert, confers a suitable consistency or form to the composition, and does not diminish the therapeutic efficacy of the compounds. The carrier is "pharmaceutically or pharmacologically acceptable" if it does not produce an adverse, allergic or other untoward reaction when administered to a mammal or human, as appropriate.

The pharmaceutical compositions containing the compounds (or salts) of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, in: *Remington's Pharmaceutical Science* (A. Gennaro, ed.), Mack Publishing Co., Easton, Pa., (1985), pp. 1492-1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosaqe Forms* 2nd Edition (1976).

The compositions of the invention for oral administration comprise an effective amount of a compound of the invention in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption.

The compounds and salts of the present invention may also be formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective amount of the composition in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide-amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methylpyrrolidinone, pluronic 60, polyoxyethylene sorbitol oleic polyesters such as poly (ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.,)(Marcel Dekker, Inc., New York, N.Y., 1980), *Reminqton's Pharmaceutical Sciences* (A. Gennaro, ed., 19th ed.)(Mack Publishing, Easton, Pa., 1995), *The United States Pharmacopeia* 24, *The National Formulary* 19, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917-927 (1963).

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

The "heterosubstituted methyl" moieties described herein are methyl groups in which the carbon atom is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety.

The "heterosubstituted acetate" moieties described herein are acetate groups in which the carbon of the methyl group is covalently bonded to at least one heteroatom and optionally with hydrogen, the heteroatom being, for example, a nitrogen, oxygen, silicon, phosphorous, boron, sulfur, or halogen atom. The heteroatom may, in turn, be substituted with other atoms to form a heterocyclo, alkoxy, alkenoxy, alkynoxy, aryloxy, hydroxy, protected hydroxy, oxy, acyloxy, nitro, amino, amido, thiol, ketals, acetals, esters or ether moiety.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

Having described the invention in detail, it will be apparent that modifications and variations are possible without departing the scope of the invention defined in the appended claims. Furthermore, it should be appreciated that all examples in the present disclosure are provided as non-limiting examples.

The following examples illustrate the invention.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Microwave Assisted Synthesis of Highly Substituted Optically Active Aminomethylated 2-Pyridones In order to obtain the nitriles as amine precursors, brominated 2-pyridones 5a-c were prepared in excellent yields (Scheme 1) using bromine in AcOH.[23] Various cyanodehalogenation procedures employing transition metal catalysts, e.g. palladium catalyzed reactions utilizing zinc cyanide as the cyanide source have worked well with aryl halides.[24,25] Unfortunately, the brominated 2-pyridone 5a was not consumed in these reactions, a fact that might be due to poisoning of the catalyst by the sulfur containing starting material. As a consequence, the attention was turned to the original Rosenmund von Braun cyanation employing CuCN in refluxing DMF and this time the desired cyanosubstituted 2-pyridones were obtained. Still, the long reaction times and the rather harsh work up procedure were not ideal resulting in low and irreproducible yields. Recent reports of alternative cyanodehalogenation reactions performed on aryl halides have shown that microwave assisted organic synthesis, MAOS, can improve this reaction significantly.[25-28] Therefore, it was investigated if this technology would be beneficial also for the Rosenmund Von Braun cyanodehalogenation. In the first attempts, 2-pyridone 5a and CuCN were dissolved in DMF and heated to 200° C. for 10 minutes in a microwave apparatus. Although product was formed, the yields were still low (<30%) and a lot of unconsumed starting material was left. Extending the reaction time to 20 minutes gave more product but also significant amounts of byproducts were formed. Fortunately by increasing the temperature to 220° C. and switching the solvent to N-methyl-2-pyrrolidinone, NMP, the cyano substituted 2-pyridone 6a was obtained without detecting any competing side reaction. However, the isolated yields did not reflect the encouraging TLC and LCMS data. The commonly applied work up procedures for the Rosenmund von Braun reaction are often harsh, e.g. heating with HCl and $FeCl_3$,[17] which clearly affected the total yield and was also a concern regarding the risk of racemisation. Therefore, after trying different extraction procedures with unsatisfactory outcomes, most of the solvent NMP was lyophilized from water. This was followed by thorough extraction of the remaining solid with $CH_2Cl_2$, which proved critical to obtain good overall yields. Final purification with column chromatography resulted in cyano-substituted 2-pyridones 6a-c (Scheme 1) in very good yields taking into account the presence of the sterically demanding naphtyl substituent in 5a and 5b.

Scheme 1.

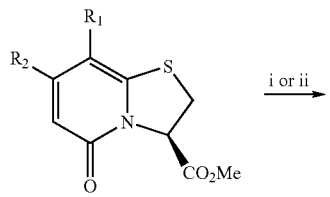

4a: $R_1$ = $CH_2$-naphtyl, $R_2$ = Ph
4b: $R_1$ = $CH_2$-naphtyl, $R_2$ = cyclopropyl
4c: $R_1$ = Ph, $R_2$ = Me

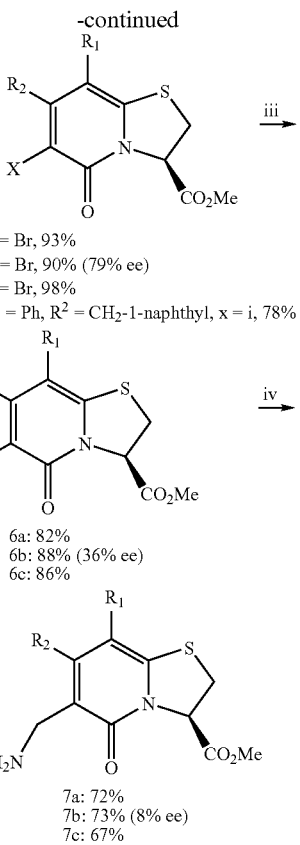

5a: X = Br, 93%
5b: X = Br, 90% (79% ee)
5c: X = Br, 98%
5d: $R^1$ = Ph, $R^2$ = $CH_2$-1-naphthyl, x = i, 78%

6a: 82%
6b: 88% (36% ee)
6c: 86%

7a: 72%
7b: 73% (8% ee)
7c: 67%

* Reagents and conditions: (i) $Br_2$, AcOH, rt gave 5a-c; (ii) N-Iodosuccinimide, AcOH:TFA, rt gave 5d; (iii) CuCN, NMP, MW 220° C, 20 min; (iv) $BH_3$•$Me_2$S, THF, MW 100° C, 1 min.

The remaining step to the desired primary amines was the reduction of the nitrile. To accomplish this transformation one had to take into account some constrains. First, sulfur-assisted $NaBH_4$ reduction of carboxylic acid esters has been reported[29] indicating that one might experience selectivity problems and over reduction to the corresponding alcohol. Secondly, Padwa and co workers have shown that transition metal catalyzed hydrogenation reactions at high pressure (90 psi) saturates the 2-pyridone skeleton.[23] Encouraged by a previous good experience in using PdO in a selective dehalogenation of iodopyridone 5d at atmospheric pressure, hydrogenation was utilized in the initial attempts to reduce the nitrile. Unfortunately, hydrogenations at atmospheric pressure using various catalysts e.g. PdO, Pd/C[30] and $PtO_2$[31] as well as different sources of hydrogen (hydrogen gas or ammonium formate) or elevated pressure at 50 psi all proved unsuccessful. Pd—S/C[32] and Rh/C[33] were also applied to investigate whether the low reactivity could be explained by the aforementioned problem with poisoning of the catalyst, but without success. Now several electrophilic reducing agents that had been reported as suitable reducing agents for nitrites such as N-Ethyl-N-isopropylaniline-borane (BACH-EI™),[34,35] $AlH_3$.$NMe_2$Et[37] and $BH_3$.$Me_2$S (BMS)[38] were tested. Again, the cyano group remained intact using both BACH-EI™ and $AlH_3NMe_2$Et, yet in the latter case the methyl ester was reduced to the corresponding alcohol according to LC-MS. The most promising result was achieved with the BMS complex in THF, where traces of the desired amine could be detected after several hours at room temperature. Refluxing overnight gave a substantial increase of product formation albeit this also yielded considerable amounts of byproducts. With the intention to improve the unsatisfactory yields and reaction times, microwave irradiation was studied as an alternative source of heating. Delightfully, this gave complete conversion of the hitherto almost inert cyano functionality in 60 seconds at 100° C. and primary amines 7a-c were obtained in good yields (Scheme 1). The optical purity, however, continued to deteriorate also during this transformation and the enantiomeric excess for primary amine 7b was only 8%.

To introduce symmetrical dialkylamines the renowned Mannich reaction was employed, a classical method known since the early 1900's,[39] often mentioned as one of the most important C—C bond forming reactions in organic chemistry.[40] Initial efforts using aqeous formaldehyde and protic solvents proved unfruitful as no aminomethylated product could be detected. However, switching to paraformaldehyde and dried aprotic solvents gave some product, still the yields were poor and a lot of unidentified byproducts were formed. These well known limitations of the Mannich reaction could possibly be diminished by shortening the reaction times and encouraged by the results from both the cyanodehalogenation and the borane dimethyl sulfide reduction of the nitrites, microwave irradiation was applied also in this reaction. Disappointingly, initial studies resulted in poor yields, at the best 28%. This could be due to slow formation of the in situ generated iminium salt, allowing competing side reactions to occur. To avoid these problems preformed methylene iminium salts were used, giving a higher concentration of the reactive species. Thus, commercially available Eschenmoser's salt ($I^-Me_2N^+=CH_2$) and pyridone 4c were irradiated for 9 minutes in 1,2-dichloroethane at 160° C. This improved the result substantially as 8a could be isolated in 78% yield. The use of preformed iminiumsalts is a well proven strategy in the Mannich reaction often known to shorten reaction times and increase yields.[40] Several methods for their preparation are available[41] and N,N-morpholine- and N,N-dimethylmethyleneammoniumchloride were prepared according to published procedures by cleavage of aminals with acetylchloride.[42] The aminals were conveniently synthesized by condensing the amine of choice with formaldehyde under aqueous conditions.[43] The methyleneammonium chloride salts proved effective and compounds 8a and 8b were isolated in 92 and 93% respectively (Table 1, entry 1 and 2). With these excellent results in hand, the microwave assisted Mannich reaction was now applied on the sterically more demanding 2-pyridones 4a,b, which required another portion of reactant and heating for an additional 400 s to be completed. Bearing in mind the pronounced steric impact of the $CH_2$-naphtyl substituent $R^2$ in 4a,b (Table 1) the isolated yields for 8c-f (48-66%) were satisfying. It has previously been observed that the dimethylmethyleneammonium salt is less reactive than the corresponding morpholineammonium salt.[41] This was also confirmed by the results obtained in this study (Table 1, entry 3 and 4). Besides resulting in good to excellent yields, this microwave assisted method offers a much faster reaction, 7-14 minutes compared to >22 hours for earlier published procedures.[19,20] Moreover, in contradiction to what was observed for the previously described microwave-assisted cyanation and reduction step, the optical purity was not affected as much during this transformation and tertiary amine 8f was obtained with an ee of 75% (compared to 79% ee for the starting material 4b).

TABLE 1

Microwave Assisted Mannich Reaction on Substituted 2-pyridones

| entry | $R^1$ | $R^2$ | $R^3$ | time (s) | product | yield (%)[a] |
|---|---|---|---|---|---|---|
| 1 | Phenyl | methyl | $NMe_2$ | 400 | 8a | 92 |
| 2 | Phenyl | methyl | morpholine | 400 | 8b | 93 |
| 3 | Phenyl | $CH_2$-1-naphtyl | $NMe_2$ | 400*2[b] | 8c | 48 |
| 4 | Phenyl | $CH_2$-1-naphtyl | morpholine | 400*2[b] | 8d | 64 |
| 5 | Cyclopropyl | $CH_2$-1-naphtyl | $NMe_2$ | 400*2[b] | 8e | 55 |
| 6 | Cyclopropyl | $CH_2$-1-naphtyl | morpholine | 400*2[b] | 8f[c] | 66 |

[a]Yield of the purified product.
[b]An additional amount of 1.1 eq iminium salt was added.
[c]The enantiomeric excess was 75% (compared to 79% ee for the starting material 4b) as determined by chiral HPLC.

Example 2

All reactions were carried out under an inert atmosphere with dry solvents under anhydrous conditions, unless otherwise stated. $CH_2Cl_2$ was freshly distilled from calcium hydride, THF was freshly distilled from potassium and N-methyl-2-pyrrolidinone (NMP) was dried over 3A molecular sieves.

All microwave reactions were carried out in a monomode reactor using Smith Process Vials™ (0.5-2.0 or 2.0-5.0 mL filling volume) sealed with Teflon septa and an aluminum crimp top.

TLC was performed on Silica Gel 60 $F_{254}$ (Merck) using UV light detection and staining with a solution of phosphomolybdic acid and cerium (IV) sulfate in 6% aqueous sulfuric acid or ninhydrin (0.2% in EtOH) and the compounds were visualized upon heating. Flash column chromatography (eluents given in brackets) employed normal phase silica gel (Matrex, 60 A, 35-70 μm, Grace Amicon). Ion-exchange resin (Amberlyst 15, $H^+$-form, 20-50 mesh) was washed with MeOH prior to use. Organic extracts were dried over sodium sulphate before being concentrated. The $^1H$ and $^{13}C$ NMR spectra were recorded at 298 K with a Bruker DRX-400 spectrometer in $CDCl_3$ [residual $CHCl_3$ ($\delta_H$ 7.26 ppm) or $CDCl_3$ ($\delta_C$ 77.0 ppm) as internal standard] or MeOH [residual $CD_2HOD$ ($\delta_H$ 3.31 ppm) or $CD_3OD$ ($\delta_C$ 49.0 ppm) as internal standard]. IR spectra were recorded on an ATI Mattson Genesis Series FTIR™ spectrometer. Optical rotations were measured with a Perkin-Elmer 343 polarimeter at 20° C. High-resolution mass spectra (EI or FAB) were recorded on a JEOL JMS-SX 102 mass spectrometer. Mass spectra of compound 7c were recorded on a Waters micromass ZG using electrospray ($ES^+$).

(3R)-6-Bromo-7-naphthalen-1-ylmethyl-5-oxo-8-phenyl-2,3-dihydro-5H-thiazolo[3,2-a]pyridine-3-carboxylic acid methyl ester (5a). $Br_2$ (110 uL, 2.1 mmol) was added dropwise to a stirred solution of 4a (1.0 g, 2.3 mmol) in AcOH (40 mL) at rt. After stirring for 10 min the reaction mixture was concentrated. Purification by silica gel chromatography (heptane:EtOAc, 1:1) gave 5b as a white foam (1.1 g, 93%): $[\alpha]_{D140}$ (c 1.0, $CHCl_3$); IR λ 2921, 2850, 1747, 1654, 1581, 1467, 1357, 1224 $cm^{-1}$; $^1H$ NMR (400 MHz, $CDCl_3$) δ 7.83 (dd, J=7.8, 1.6, 1H), 7.76-7.69 (m, 2H), 7.48-7=(m, 3H), 7.20-6.94 (m, 6H), 5.78 (dd, J=8.6, 2.6, 1H), 4.38-4.24 (m, 2H), 3.89 (s, 3H), 3.73 (dd, J=11.8, 8.6, 1H), 3.50 (dd, J=11.8, 2.6, 1H); $^{13}C$ NMR (100 MHz, $CDCl_3$) δ 168.1, 157.7, 152.2, 146.2, 136.1, 133.6, 132.5, 131.5, 129.7, 129.2, 128.7, 128.6 (broad and splitted), 128.5, 127.0, 125.9, 125.5, 125.4, 124.4, 122.8, 117.0, 114.4, 64.9, 53.5, 37.2, 31.7; HRMS (FAB+) calcd for $C_{27}H_{20}BrNO_3S$ 506.0426, obsd 506.0427.

6-Bromo-7-(naphtalen-1-ylmethyl)-5-oxo-8-cyclopropyl-2,3-dihydro-5H-thiazolo[3,2-a]pyridine-3-carboxylic Acid Methyl Ester (5b). $Br_2$ (28 uL, 0.54 mmol) was added dropwise to a stirred solution of 4b (200 mg, 0.51 mmol) in AcOH (6 mL) at rt. After stirring for 30 min the reaction was quenched with 10% aqueous $Na_2S_2O_5$ and the solution was extracted with $CH_2Cl_2$. The organic layers were washed with 10% aqueous $NaHCO_3$ and brine and the resulting aqueous layers were combined and re-extracted with $CH_2Cl_2$. The combined organic layers were dried ($Na_2SO_4$), filtered and concentrated. Purification by silica gel chromatography (heptane:EtOAc, 1:4) gave 5b as a white foam (217 mg, 90%). $[\alpha]_{D177}$ (c 1.0, $CHCl_3$); IR λ 2996, 2950, 2356, 1752, 1639, 1209, 790; $^1H$ NMR (400 MHz, $CDCl_3$) 8.16 (d, J=8.2 Hz, 1H), 7.90 (d, J=8.1 Hz, 1H), 7.74 (d, J=8.4 Hz, 1H), 7.64-7.51 (m, 2H), 7.31 (t, 1H), 6.86 (d, J=6.9 Hz, 1H), 5.72 (dd, J=6.2, 2.5 Hz, 1H), 4.88-4.74 (m, 2H), 3.85 (s, 3H), 3.72 (dd, J=11.8, 8.7 Hz, 1H), 3.57-3.51 (dd, J=9.3, 2.4 Hz, 1H), 1.44-1∓(m, 1H), 0.73-0.63 (m, 2H); 0.59-0.50 (m, 2H); $^{13}C$ NMR (100 MHz, $CDCl_3$) 168.3, 157.6, 154.4, 146.6, 133.8, 132.4, 131.8, 128.9, 127.1, 126.2, 125.7, 125.6, 123.8, 122.9, 114.7, 114.4, 64.0, 53.4, 36.6, 31.6, 12.2, 7.7, 7.3; HRMS (FAB+) calcd for $C_{23}H_{21}BrNO_3S$ 470.0420, obsd 470.0439.

(3R)-6-Bromo-7-methyl-5-oxo-8-phenyl-2,3-dihydro-5H-thiazolo[3,2-a]pyridine-3-carboxylic acid methyl ester (5c). By following the procedure described for the preparation of 5a from 4a, 4c (400 mg, 1.3 mmol) gave 5c as a white foam (500 mg, 98%): $[\alpha]_{D213}$ (c 1.0, $CHCl_3$); IR λ 2998, 2950, 1745, 1639, 1579, 1471, 1429, 1211 $cm^{-1}$; $^1H$ NMR (400 MHz, $CDCl_3$) δ 7.46-7.32 (m, 3H), 7.24-7.15 (m, 2H), 5.67 (dd, J=8.6, 2.4, 1H), 3.80 (s, 3H), 3.67 (dd, J=11.7, 8.6, 1H), 3.42 (dd, J=11.8, 2.4, 1H), 2.10 (s, 3H); $^{13}C$ NMR (100 MHz, $CDCl_3$) δ 168.1, 157.2, 150.4, 145.1, 136.7, 129.9, 129.6, 128.9, 128.8, 128.4, 116.2, 112.5, 64.6, 53.3, 31.6, 22.1; HRMS (FAB+) calcd for $C_{16}H_{15}BrNO_3S$ 378.9956, obsd 378.9947.

(3R)-6-Iodo-7-naphthalen-1-ylmethyl-5-oxo-8-phenyl-2,3-dihydro-5H-thiazolo[3,2-a]pyridine-3-carboxylic acid methyl ester (5d). N-Iodosuccinimide (125 mg, 0.56 mmol) was added to a stirred solution of 4a (100 mg, 0.23 mmol) in AcOH (1 mL) and TFA (50 μl) at rt. After stirring for 24 hours the reaction mixture was poured on ice water and neutralized with aqueous saturated $NaHCO_3$. The precipitate was filtered off and purified by silica gel chromatography (heptane:EtOAc, 1:1) giving 5d as a pale orange solid (97 mg, 78%): $[\alpha]_D$ 176 (c 0.65, $CHCl_3$); IR λ 2360, 2344, 1747, 1635, 1570, 1458, 1211, 1151, 993 $cm^{-1}$; $^1H$ NMR (400 MHz, $CDCl_3$) δ 7.82 (d, J=7.8, 1H), 7.71 (m, 2H), 7.48-7–(m, 3H), 7.21-7.01 (m, 5H), 6.97 (d, J=7.5, 1H), 5.77 (dd, J=8.7, 2.4, 1H), 4.42-4.28 (m, 2H), 3.87 (s, 3H), 3.71 (dd, J=11.8, 8.7, 1H), 3.43 (dd, J=11.8, 2.4, 1H); $^{13}C$ NMR (100 MHz, $CDCl_3$) δ 168.1, 158.7, 156.5, 147.6, 136.3, 133.5, 132.5, 131.5, 129.6, 129.1, 128.6, 128.5 (broad and splitted), 128.3, 127.0, 125.8, 125.5, 125.3, 124.5, 122.7, 117.1, 94.3, 65.2, 53.4, 42.0, 31.7; HRMS (FAB+) calcd for $C_{26}H_{21}INO_3S$ 554.0287, obsd 554.0303.

(3R)-6-Cyano-7-naphthalen-1-ylmethyl-5-oxo-8-phenyl-2,3-dihydro-5H-thiazolo[3,2-a]pyridine-3-carboxylic acid methyl ester (6a). CuCN (120 mg, 1.3 mmol) was added to a stirred solution of 5a (150 mg, 0.30 mmol) in NMP (1.0 mL) at rt. The reaction mixture was heated at 220° C. for 20 min using microwave irradiation and the solvent was then removed by lyophilisation from deionised water. The residue was thoroughly extracted with $CH_2Cl_2$, dried and concentrated. Purification by silica gel chromatography (heptane:EtOAc, 1:1) gave 6a as a white foam (110 mg, 82%)$[\alpha]_D$ –83 (c 1.0, $CHCl_3$); IR λ 3012, 2956, 2217, 1751, 1654, 1486, 1442, 1369 $cm^{-1}$; $^1H$ NMR (400 MHz, $CDCl_3$) δ 7.79 (d, J=7.8, 1H), 7.70 (d, J=8.1, 1H), 7.62 (d, J=8.2, 1H), 7.47-7.29 (m, 3H), 7.19-6.92 (m, 5H), 6.87 (d, J=7.3, 1H), 5.79 (dd, J=8.9, 2.3, 1H), 4.41-4.27 (m, 2H), 3.89 (s, 3H), 3.75 (dd, J=11.9, 8.9, 1H), 3.52 (dd, J=11.9, 2.3, 1H); $^{13}C$ NMR (100 MHz, $CDCl_3$) δ 167.6, 160.7, 158.7, 155.2, 134.4, 133.6, 132.4, 131.4, 129.7, 129.2, 128.8 (broad and splitted), 128.6, 127.6, 126.1, 125.7, 125.3, 125.2, 122.7, 117.1, 115.2, 101.3, 64.4, 53.7, 35.3, 31.8; HRMS (EI+) calcd for $C_{27}H_{20}N_2O_3S$ 452.1195, obsd 452.1192.

6-Cyano-7-(naphtalen-1-ylmethyl)-5-oxo-8-cyclopropyl-2,3-dihydro-5H-thiazolo[3,2-a]pyridine-3-carboxylic Acid Methyl Ester (6b). By following the procedure described for the preparation of 6a from 5a, 5b (100 mg, 0.21 mmol) gave 6b as a white foam (78 mg, 88%). $[\alpha]_D$ –44 (c 1.0, $CHCl_3$); IR λ 3004, 2954, 2360, 2213, 1747, 1644, 1481, 1213, 1164, 792; $^1H$ NMR (400 MHz, $CDCl_3$) 8.12 (d, J=8.2 Hz, 1H), 7.89 (d, J=7.9 Hz, 1H), 7.75 (d, J=8.7 Hz, 1H), 7.62-7.51 (m, 2H), 7.34 (t, 1H), 6,89 (d, J=7.1 Hz, 1H) 5.74 (dd, J=6.7, 2.2 Hz, 1H)=9.8, 2.2 Hz, 1H), 1.27-1.21 (m, 1H), 0.69-0.65 (m, 2H); 0.55-0.53 (m, 2H): $^{13}$C NMR (100 MHz, CDCl$_3$) (167.7, 162.9, 158.6, 155.6, 133.8, 132.4, 131.7, 128.9, 127.6, 126.4, 125.9, 125.5, 124.1, 122.8, 115.2, 114.5, 101.7, 63.5, 53.6, 34.8, 31.7, 11.3, 7.7, 7.2; HRMS (FAB+) calcd for $C_{24}H_{21}N_2O_3S$ 417.1267, obsd 417.1289.

(3R)-6-Cyano-7-methyl-5-oxo-8-phenyl-2,3-dihydro-5H-thiazolo[3,2-a]pyridine-3-carboxylic acid methyl ester (6c). By following the procedure described for the preparation of 6a from 5a, 5c (150 mg, 0.39 mmol) gave 6c as a pale yellow foam (110 mg, 86%): $[\alpha]_D$–161 (c 1.0, CHCl$_3$); IR λ 3012, 2956, 2215, 1749, 1648, 1440, 1365, 1257, 1216 cm$^{-1}$. $^1$H NMR (400 MHz, CDCl$_3$) δ 7.50-7.39 (m, 3H), 7.25-7~(m, 2H), 5.72 (dd, J=8.8, 2.3, 1H), 3.85 (s, 3H), 3.72 (dd, J=11.9, 8.8, 1H), 3.51 (dd, J=11.9, 2.3, 1H), 2.21 (s, 3H); $^{13}$C NMR (100 MHz, CDCl$_3$) δ 167.6, 158.8, 158.4, 154.3, 135.0, 129.7, 129.5, 129.1 (splitted), 128.9, 116.5, 115.4, 99.5, 64.1, 53.5, 31.7, 20.0; HRMS (FAB+) calcd for $C_{17}H_{15}N_2O_3S$ 327.0803, obsd 327.0805.

(3R)-6-Aminomethyl-7-naphthalen-1-ylmethyl-5-oxo-8-phenyl-2,3-dihydro-5H-thiazolo[3,2-a]pyridine-3-carboxylic acid methyl ester (7a). BH$_3$.Me$_2$S (250 μL, 2M in THF, 0.5 mmol) was added dropwise to a solution of 6a (50 mg, 0.11 mmol) in dry THF (4 mL) at rt. The reaction vessel was sealed and heated for 60 s at 100° C. using microwave irradiation. The reaction mixture was cooled to room temperature, diluted with CH$_2$Cl$_2$, poured onto ice-cold aqueous HCl (1M) and agitated. The pH was then adjusted to ~10 with 2M aqueous NaOH and the aqueous layer was extracted with CH$_2$Cl$_2$. The combined organic layers were dried and concentrated. The crude product was dissolved in MeOH and swirled with Amberlyst 15. The solid phase was transferred to a filtration funnel and washed with MeOH. The product was released by addition of 10% NH$_3$ in MeOH and eluted with MeOH. Concentration of the filtrate gave 7a as a yellow solid (36 mg, 72%): $[\alpha]_D$–44 (c 0.25, CHCl$_3$); IR λ 2958, 2854, 1747, 1631, 1492, 1440, 1259, 1214 cm$^{-1}$; $^1$H NMR (400 MHz, CDCl$_3$) δ 7.83 (d, J=8.2, 1H), 7.78 (d, J=8.1, 1H), 7.71 (d, J=8.7, 1H), 7.54-7.00 (m, 9H), 5.74 (dd, J=8.6, 2.7, 1H), 4.25-4.11 (m, 2H), 3.96-3.51 (m, 8H), 3.48 (dd, J=11.8, 2.7, 1H); $^{13}$C NMR (100 MHz, CDCl$_3$) δ 168.1, 161.3, 153.5, 148.9, 135.8, 133.8, 133.6, 131.2, 129.7, 129.3, 128.7 (splitted), 128.5 (splitted), 127.3, 126.3, 125.9, 125.5, 124.4, 123.2, 118.4, 116.6, 64.2, 53.6, 38.0, 33.2, 31.7; HRMS (FAB+) calcd for $C_{27}H_{24}N_2NaO_3S$ 479.1405, obsd 479.1405.

(3R)-6-Aminomethyl-8-cyclopropyl-7-naphthalen-1-ylmethyl-5-oxo-2,3-dihydro-5H-thiazolo[3,2-a]pyridine-3-carboxylic acid methyl ester (7b). By following the procedure described for the preparation of 7a from 6a, 6b (46 mg, 0.11 mmol) gave 7b as a yellow solid (33 mg, 73%): $[\alpha]_D$–64 (c 0.25, CHCl$_3$); IR λ 2952, 1747, 1631, 1569, 1504, 1259, 1214 cm$^{-1}$; $^1$H NMR (400 MHz, CDCl$_3$) δ 8.18 (d, J=8.2, 1H), 7.94-7.27 (m, 5H), 6.81 (d, J=6.8, 1H), 5.67 (d, J=7.3, 1H), 4.77-100 MHz, CDCl$_3$) δ 168.3, 161.1, 155.6 149.5, 133.7, 133.7, 131.6, 128.7, 127.3, 126.4, 126.0, 125.5, 123.8, 123.4, 116.9, 115.7, 63.4, 53.5, 37.6, 32.6, 31.6, 11.8, 7.2, 7.1; HRMS (FAB+) calcd for $C_{24}H_{25}N_2O_3S$ 421.1586, obsd 421.1593.

(3R)-6-Aminomethyl-7-methyl-5-oxo-8-phenyl-2,3-dihydro-5H-thiazolo[3,2-a]pyridine-3-carboxylic acid methyl ester (7c). By following the procedure described for the preparation of 7a from 6a, 6c (36 mg, 0.11 mmol) gave 7c as a yellow solid (27 mg, 67%): $[\alpha]_D$–110 (c 0.13, CHCl$_3$); IR λ 2956, 1747, 1631, 1575, 1490, 1442, 1216 cm$^{-1}$; $^1$H NMR (400 MHz, CDCl$_3$) δ 7.49-7+(m, 3H), 7.25-7.15 (m, 2H), 5.64 (dd, J=8.5, 2.4, 1H), 3.92-3.69 (m, 7H), 3.62 (dd, J=11.5, 8.6, 1H), 3.41 (dd, J=11.6, 2.3, 1H), 2.02 (s, 3H); $^{13}$C NMR (100 MHz, CDCl$_3$) 6168.8, 161.1, 152.0, 147.8, 136.4, 130.0, 129.9, 129.0, 128.9, 128.5, 118.0, 115.3, 64.0, 53.6, 37.9, 31.7, 18.0; MS (ES+) calcd 331 for $C_{17}H_{20}N_2O_3S$, obsd 331.

6-Dimethylamine-7-(methyl)-5-oxo-8-phenyl-2,3-dihydro-5H-thiazolo[3,2-a]pyridine-3-carboxylic Acid Methyl Ester (8a). N,N-Dimethylmethyleneammoniumchloride (140 mg, 1.50 mmol) was added to a stirred solution of 4c (200 mg, 0.66 mmol) in dry 1,2-dichloroethane (3 mL) at rt. The reaction vessel was sealed and heated for 400 s at 140° C. using microwave irradiation. The reaction mixture was then diluted with CH$_2$Cl$_2$, MeOH and concentrated. Purification by silica gel chromatography (ethylacetate→ethylacetate 2.5% triethylamine) gave 8a as a white foam (219 mg, 92%). $[\alpha]_D$– 163 (c 1.0, CHCl$_3$); IR λ 2939, 2817, 1747, 1631, 1490, 1209, 703; $^1$H NMR (400 MHz, CDCl$_3$) 7.43-7.30 (m, 3H) 7.24-7≠ (m, 2H) 5.64 (dd, J=8.6, 2.5 Hz, 1H) 3.78 (s, 3H) 3.59 (dd, J=11.7, 8.7 Hz, 1H) 3.47 (d, J=12.2 Hz, 1H) 3.38 (dd, J=11.7, 2.5 Hz, 1H) 3.31 (d,J=12.2 Hz, 1 H) 2.25 (s, 6 H) 2.0 (s, 3H); $^{13}$C NMR (100 MHz, CDCl$_3$) 168.6, 161.5, 150.7, 144.2, 137.3 130.0, 129.7, 128.7, 128.6, 127.9, 122.2, 116.7, 64.0, 54.2, 53.1, 45.4, 31.3; 17.5; IR λ 2939, 2817, 1747, 1631, 1490, 1209, 703; HRMS (FAB+) calcd for $C_{19}H_{23}N_2O_3S$ 359.1429, obsd 359.1426.

6-Morpholine-7-(methyl)-5-oxo-8-phenyl-2,3-dihydro-5H-thiazolo[3,2-a]pyridine-3-carboxylic Acid Methyl Ester (8b). By following the procedure described for the preparation of 8a from N,N-Dimethylmethyleneammoniumchloride and 4c, N,N-Morpholinemethyleneammoniumchloride and 4c (200 mg, 0.66 mmol) gave 8b as a white foam (249 mg, 93%). $[\alpha]_D$–161 (c 1.0, CHCl$_3$); IR λ 2955, 2850, 2360, 1749, 1631, 1490, 1112, 703; $^1$H NMR (400 MHz, CDCl$_3$) 7.45-7.34 (m, 3H), 7.26-7.20 (m, 2H), 5.67 (dd, J=8.6, 2.6 Hz, 1H), 3.82 (s, 3H), 3.70-3.64 (m, 4H), 3.63-3.53 (m, 2H), 3.46-3.38 (m, 2H), 2.53-2.48 (m, 4H), 2.07 (s, 3H); $^{13}$C NMR (100 MHz, CDCl$_3$) 168.5, 161.5, 151.3, 144.4, 137.2, 130.0, 129.8, 128.7, 128.6, 120.0, 121.1, 116.7, 67.1, 64.0, 53.4, 53.1, 31.8, 31.3; 17.5; HRMS (FAB+) calcd for $C_{21}H_{25}N_2O_4S$ 401.1535, obsd 401.1536.

6-Dimethylamine-7-(naphtalen-1-ylmethyl)-5-oxo-8-phenyl-2,3-dihydro-5H-thiazolo[3,2-a]pyridine-3-carboxylic Acid Methyl Ester (8c). N,N-Dimethylmethyleneammoniumchloride (144 mg, 1.54 mmol) was added to a stirred solution of 4a (300 mg, 0.70 mmol) in dry 1,2-dichloroethane (3 mL) at rt. The reaction vessel was sealed and heated for 140° C. for 400 s using microwave irradiation, more N,N-Dimethylmethyleneammoniumchloride (72 mg, 0.77 mmol) was added, and the reaction mixture was heated for another 400 s at 140° C. The reaction mixture was then diluted with CH$_2$Cl$_2$, MeOH and concentrated. Purification by silica gel chromatography (ethylacetate→ethylacetate 2.5% triethylamine) gave 8c as a white foam (148 mg, 48%). $[\alpha]_D$–151 (c 1.0, CHCl$_3$); IR λ 3048, 2940, 2817, 2767, 1747, 1633, 1490, 790, 701; $^1$H NMR (400 MHz, CDCl$_3$) 7.83-7.77 (m, 2H) 7.67 (d, J=8.2 Hz, 1H) 7.45-7.30 (m, 3H) 7.12-6.99 (m, 6H) 5.76 (dd, J=8.6, 2.6 Hz, 1H) 4.44 (d, J=16 Hz, 1H) 4.32 (d, J=16 Hz, 1H) 3.85 (s, 3H) 3.66 (dd, J=11.8, 8.7 Hz, 1H) 3.44 (dd, J=11.8, 8.7 Hz, 1H) 3.30-3.20 (m, 2H) 2<(s, 6H); $^{13}$C NMR (100 MHz, CDCl$_3$) 168.5, 161.8 152.2, 145.5, 136.5, 134.5, 133.3, 131.6, 129.8, 129.2, 128.4, 128.3, 128.2, 127.9, 126.7, 125.8, 125.4, 125.3, 124.2, 123.4, 122.8, 117.2, 64.2, 53.9, 53.1, 45.6, 31.8, 31.3; HRMS (FAB+) calcd for $C_{29}H_{29}N_2O_4S$ 485.1893, obsd 485.1866.

6-Morpholine-7-(naphtalen-1-ylmethyl)-5-oxo-8-phenyl-2,3-dihydro-5H-thiazolo[3,2-a]pyridine-3-carboxylic Acid Methyl Ester (8d). N,N-Morpholinemethyleneammoniumchloride (209 mg, 1.54 mmol) was added to a stirred solution of 4a (300 mg, 0.70 mmol) in dry 1,2-dichloroethane (3.2 mL) at rt. The reaction vessel was sealed and heated for 400 s at 140° C. using microwave irradiation, more N,N-Morpholinemethyleneammoniumchloride (105 mg, 0.77 mmol) was added and the reaction mixture was heated for another 400 s at 140° C. The reaction mixture was then diluted with $CH_2Cl_2$, MeOH and concentrated. Purification by silica gel chromatography (ethylacetate→ethylacetate 2.5% triethylamine) gave 8d as a yellow foam (237 mg, 64%). $[\alpha]_D$ –98 (c 1.0, $CHCl_3$); IR λ 2952, 2846, 1749, 1633, 1490, 1112, 701 cm$^{-1}$; $^1$H NMR (400 MHz, $CDCl_3$) δ 7.84-7.79 (m, 2H) 7.68 (d, J=8.2 Hz, 1H) 7.46-7.38 (m, 2H) 7.34 (t, 1H) 7.17-7.04 (m, 6H) 5.75 (dd, J=8.6, 2.7 Hz, 1H) 4.49 (d, J=15.9, 1H) 4.34 (d, J=15.9 Hz, 1H) 3.87 (s, 3H) 3.69 (dd, J=11.8, 8.7 Hz, 1H) 3.56-3.50 (m, 4H) 3.46 (dd, J=11.8, 2.7 Hz, 1H) 3=(m, 2H) 2.40-2.30 (m, 4H); $^{13}$C NMR (100 MHz, $CDCl_3$) δ 168.5, 161.9, 153.1, 145.7, 136.5, 134.8, 133.4, 131.7, 129.9, 129.3, 128.6, 128.4, 128.4, 128.0, 126.7, 125.8, 125.5, 125.4, 124.4, 122.8, 122.3 117.5, 66.9, 64.3, 53.5, 53.2, 53.2, 32.0, 31.3; HRMS (FAB+) calcd for $C_{31}H_{31}N_2O_4S$ 527.1999, obsd 527.2008.

6-Dimethylamine-7-(naphtalen-1-ylmethyl)-5-oxo-8-cyclopropyl-2,3-dihydro-5H-thiazolo[3,2-a]pyridine-3-carboxylic Acid Methyl Ester (8e). By following the procedure described for the preparation of 8c from 4a, 4b (200 mg, 0.51 mmol) gave 8e as a white foam (125 mg, 55%). $[\alpha]_D$ –177 (c 1.0, $CHCl_3$); IR λ 2939 2948, 2817, 2767, 1747, 1633, 1579, 1498, 1211, 792, 773; $^1$H NMR (400 MHz, $CDCl_3$) 8.23 (d, J=8.4 Hz, 1H), 7.86 (d, J=7.8 Hz, 1H) 7.69 (d, J=8.2 Hz, 1H) 7.60-7.48 (m, 2H) 7.31-27 (m, 1H) 6.82 (d, J=6.8 Hz, 1H) 5.69 (dd, J=8.7, 2.5 Hz, 1H) 4.83-4.80 (m, 2H) 3∥(s, 3H) 3.67 (dd, J=11.8, 8.7 Hz, 1H) 3.48 (dd, J=8.7, 2.6 Hz, 1H) 3.30-3.19 (m, 2H) 2.19 (s, 6H) 1.34-1.24 (m, 1H) 0.63-0.53 (m, 4H);

$^{13}$C NMR (100 MHz, $CDCl_3$) 168.7, 161.7, 154.9, 145.9, 134.5, 133.5, 131.9, 128.6, 128.6, 126.0, 125.6, 125.5, 123.7, 123.6, 123.0, 114.2, 63.4, 53.7, 53.0, 45.5, 31.2, 31.2, 11.5, 7.2, 7.0; HRMS (FAB+) calcd for $C_{26}H_{29}N_2O_3S$ 449.1893, obsd 449.1887.

6-Morpholine-7-(naphtalen-1-ylmethyl)-5-oxo-8-cyclopropyl-2,3-dihydro-5H-thiazolo[3,2-a]pyridine-3-carboxylic Acid Methyl Ester (8f). By following the procedure described for the preparation of 8d from 4a, 4b (400 mg, 1.02 mmol) gave 8f as a yellow foam (331 mg, 66%). $[\alpha]_D$ –110 (c 1.0, $CHCl_3$); IR λ 2956, 2844, 1749, 1631, 1496, 1110, 792, 773, 728; $^1$H NMR (400 MHz, $CDCl_3$) 8.20 (d, J=8.4 Hz, 1H), 7.87 (d, J=7.5 Hz, 1H) 7.70 (d, J=8.2 Hz, 1H) 7.61-7.48 (m, 2H) 7.29 (t, 1H) 6.84 (d, J=7.1 Hz, 1H) 5.68 (dd, J=8.7, 2.6 Hz, 1H) 4.87-4.78 (m, 2H) 3.82 (s, 3H) 3.69 (dd, J=11.8, 8.7 Hz, 1H) 3.52-3.45 (m, 5H) 3=(m, 2H) 2.34 (m, 4H) 1.40-1.32 (m, 2H) 0.68-0.53 (m, 4H); $^{13}$C NMR (100 MHz, $CDCl_3$) 168.6, 161.8, 155.5, 146.1, 134.7, 133.5, 131.9, 128.7, 126.6, 126.0, 125.6, 125.4, 123.6, 122.9, 122.4, 114.5, 66.9, 63.4 53.3, 53.1, 52.9, 31.4, 31.2, 11.5, 7.3, 7.0; HRMS (FAB+) calcd for $C_{29}H_{31}N_2O_4S$ 491.1999, obsd 491.1998.

Scheme 2:

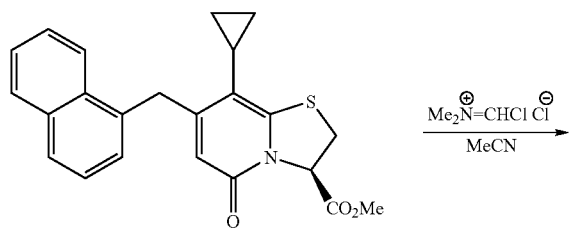

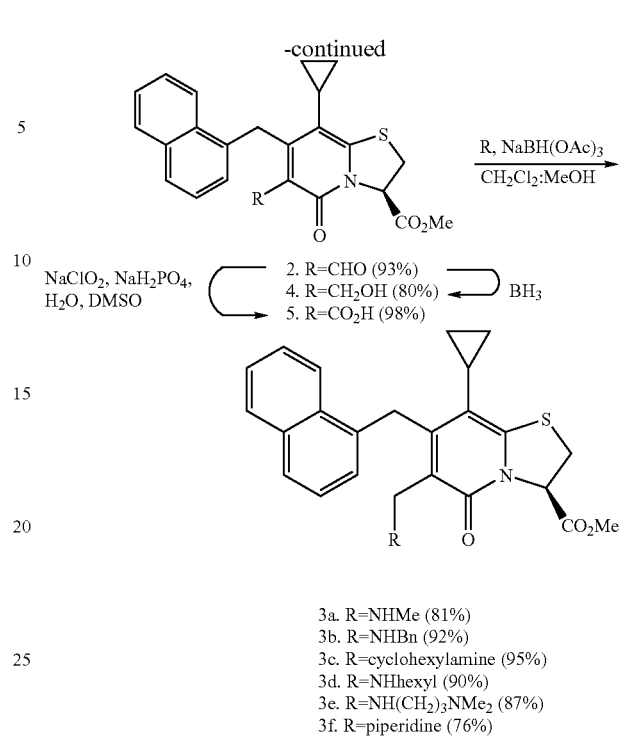

3a. R=NHMe (81%)
3b. R=NHBn (92%)
3c. R=cyclohexylamine (95%)
3d. R=NHhexyl (90%)
3e. R=NH(CH$_2$)$_3$NMe$_2$ (87%)
3f. R=piperidine (76%)

8-Cyclopropyl-6formyl-7-naphthalen-1-ylmethyl-5-oxo-2,3-dihydro-5h-thiazolo[3,2-a]pyridine-3-carboxylic acid methyl ester (2). 1 (500 mg, 1,23 mmol) was quickly added to a stirred solution of Vilsmeier's salt (Cl$^-$Me2N=CHCl) (630 mg, 4,93 mmol) in acetonitrile (10 ml). After refluxing for 3 h the solution was concentrated then diluted with $CH_2Cl_2$ and quenched with sat NaHCO$_3$ (aq). The aqueous phase was extracted with $CH_2Cl_2$ and the combined organic-phases were dried over Na$_2$SO$_4$(s) filtered and concentrated. Purification by filtering through a short silica plug (EtOAc) gave 2a as yellow foam (532 mg, 99%).$[\alpha]_D$ –16.4°; $^1$H-NMR (400 MHz, $CDCl_3$), 10.39 (s, 1H), 8·(d, J=8.3, 1H), 7.86 (d, J=8.1, 1H), 7.69 (d, J=8.3, 1H), 7.59 (t, J=7.6, 1H), 7.52 (t, J=7.4, 1H), 7.27 (t, J=7.7, 1H), 6.77 (d, J=7.0, 1H), 5.75 (dd, J=9.0, 2.6, 1H), 5.21 (d, J=14.8, 1H), 5.09 (d, J=14.8, 1H), 3.87 (s, 3H), 3.69-3.79 (m, 1H), 3.54 (dd, J=12.0, 2.5, 1H), 1.30-1.38 (m, 1H), 0.64-0.75 (m, 2H), 0.50-0.58 (m, 2H); $^{13}$C-NMR (100 MHz, $CDCl_3$), 190.7, 168.1, 162.2, 160.8, 156.7, 134.5, 133.6, 132.0, 128.7, 126.7, 126.0, 125.6, 125.3, 123.1, 123.0, 118.9, 115.5, 63.3, 53.4, 31.4, 31.4, 11.1, 7.8, 7.2; IR, 2952, 2362, 2246, 1749, 1635, 1475, 1409, 1216, 1160, 728.

General procedure for reductive anination. 1.0 eq of amine is added to a stirred solution of aldehyde in $CH_2Cl_2$:MeOH and 3 A mol sieves at 0° C. and is allowed to stir for 30 min. 1.8 eq of Sodium triacetoxyborohydride is then added and the mixture is allowed to attain rt and stir for 3 hours. Washed with sat NaHCO$_3$ (aq). The aqueous phase is extracted with $CH_2Cl_2$ and the combined organic-phases were dried over Na$_2$SO$_4$(s). Purification by column chromatography yields the aminomethylated 2-pyridones 3a-f.

(3R)-6-(Benzylamino-methyl)-8-cyclopropyl-7-(Naphtalen-1-ylmethyl)-5-oxo-2,3-dihydro-5h-thiazolo[3,2-a]pyridine-3-carboxylic Acid Methyl Ester (3b). $^1$H-NMR (400 Mhz, $CDCl_3$) 8.08 (d, J=8.32 Hz, 1H, ArH), 7.88 (d, J=7.87 Hz, 1H, ArH), 7.71 (d, J=8.14 Hz 1H, ArH), 7.64-7.47 (m, 2H, ArH) 7.35-7.07 (m, 6H, ArH) 6.83 (d, J=6.86 Hz, 1H, ArH), 5.68 (d, J=7.50 Hz, 1H, CHCO$_2$Me), 4.66 (d, J=16.47 Hz, 1H, Nph-CH$_2$), 4.57 (d, J=16.47 Hz, 1H, Nph-CH$_2$) 3.83 (s, 3H, CH$_3$) 3.77-3.38 (m, 7H, SCH$_2$, PhCH$_2$, BnNHCH$_2$) 1.46-1.33 (m, 1H, CH-cyclopropyl) 0.70-0.44 (m, 4H, CH2-cyklopropyl) 13C-NMR (100 Mhz, CDCl$_3$) δ 168.67, 161.52, 153.13, 146.01, 139.55, 134.42, 133.61, 131.74, 128.76, 128.21, 128.13, 126.94, 126.81, 126.21, 125.77, 125.50, 124.35, 123.99, 123.04, 114.53, 63.31, 53.46, 53.23, 45.31, 31.93, 31.42, 29.65, 11.79, 7.42, 7.12.

(3R)-8-Cyclopropyl-6-hydroxymethyl-7-(Naphtalen-1-ylmethyl)-5-oxo-2,3-dihydro-5h-thiazolo[3,2-a]pyridine-3-carboxylic Acid Methyl Ester (4). The formylated 2-pyridone 2 (100 mg, 0.239 mmol) was dissolved in tetrahydrofuran (3.30 mL) at 0° C. Then 2M BH$_3$.DMS.THF (0.131 mL, 0.262 mmol) was added dropwise during 15 min. The mixture was then stirred in room temperature during 1 h, quenched with methanol and concentrated twice from methanol. The residue was purified through flash column chromatography (CH$_2$Cl$_2$:MeOH, 9:1). Co-concentration from CH$_2$Cl$_2$ (×2) resulted in 4 as white foam (80.6 mg, yield: 80%). $^1$H-NMR (400 Mhz, CDCl$_3$) δ 8.16 (d, J=8.23 Hz, 1H, ArH), 7.87 (d, J=7.96 Hz, 1H, ArH), 7.71 (d, J=8.14 Hz 1H, ArH), 7.64-7.48 (m, 2H, ArH) 7+(m, 1H, ArH) 6.83 (d, J=6.95 Hz, 1H, ArH), 5.68 (d, J=7.04 Hz, 1H, CHCO2Me), 4.72 (d, J=16∞Hz, 1H, Nph-CH2), 4.61 (d, J=16.28 Hz, 1H, Nph-CH2) 4.58-4∓(m, 2H, CH$_2$OH) 3.84 (s, 3H, CH$_3$) 3.76-3.62 (m, 2H, SCH$_2$, OH) 3.60-3.50 (m, 1H, SCH$_2$) 1.46-1.34 (m, 1H, CH-cyclopropyl) 0.65 (ss, 2H, CH$_2$-cyclopropyl) 0.51 (ss, 2H, CH$_2$-cyklopropyl) $^{13}$C-NMR (100 Mhz, CDCl$_3$) δ 168.61, 161.87, 152.08, 146.62, 134.11, 133.76, 131.77, 128.94, 127.17, 126.37, 125.92, 125.66, 125.63, 124.26, 122.98, 114.93, 63.27, 58.78, 53.40, 31.77, 31.58, 11.81, 7.53, 7.20.

(3R)-8-Cyclopropyl-7-(Naphtalen-1-ylmethyl)-5-oxo-2,3-dihydro-5H-thiazolo[3,2-a]pyridine-3,6-dicarboxylic Acid 3-Methyl Ester (5). To a solution of 2 (100 mg, 0.239 mmol) in dimethylsulfoxide (2.40 mL), NaH2PO4 (66.0 mg, 0.478 mmol), dissolved in water (0.960 mL), was added dropwise at room temperature. The mixture was then kept on ice and NaClO$_2$ (86.0 mg, 0.956 mmol) dissolved in water (0.480 mL), was added dropwise during 30 min. A white precipitate formed. The reaction mixture was stirred in room temperature for 1 h and then poured into a separation funnel containing ice-cooled 1M HCl. The aqueous phase was extracted with CH$_2$Cl$_2$ and the combined organic phases concentrated. The residue was dissolved in H$_2$O:MeCN, 8:2 and freeze dried to yield 5 as a white powder (102 mg, yield: 98%). $^1$H-NMR (400 Mhz, CDCl$_3$) δ 14.60 (s, 1H, CO$_2$H), 8.21 (d, J=8.32 Hz, 1H, ArH), 7.85 (d, J=7.68 Hz 1H, ArH), 7.67 (d, J=8.14 Hz, 1H, ArH) 7.61-7.45 (m, 2H, ArH) 7.30-7.21 (m, 1H, ArH), 6.69 (d, J=6.72 Hz, 1H, ArH), 5.78 (d, J=8.42 Hz, 1H, ArH), 5.51 (d, J=14.55 Hz, 1H, Nph-CH$_2$) 5.37 (d, J=14.55 Hz, 1H, Nph-CH$_2$) 3.87 (s, 3H, CH$_3$) 3.82-3.72 (m, 1H, SCH$_2$) 3.63-3.54 (m, 1H, SCH$_2$) 1.44-1.32 (m, 1H, CH-cyclopropyl) 0.81-0.64 (m, 2H) 0.56 (sd, 2H, CH$_2$-cyclopropyl) $^{13}$C-NMR (100 Mhz, CDCl$_3$) δ 167.59, 165.24, 165.09, 163.75, 154.33, 134.92, 133.84, 132.16, 128.83, 126.78, 126.15, 125.76, 125.51, 123.40, 123.23, 118.68, 112.72, 64.10, 53.84, 33.35, 31.58, 12.10, 8.35, 7.67.

Example 3

Protocol for Hemagglutination Assay

The Hemagglutination Assay was carried out according to the following steps:

1. The bacterial culture or protein was induced with either IPTG or arabinose for an optimal amount of time.
2. Next, blood was washed with PBS (by adding PBS, spinning, pouring off supernatant, then adding PBS) until the supernatant was clear of red color.
3. The blood was then brought to optical density of 2.0 at a wavelength of 640 nm to absorbance of 1.8-2.0 (PBS was added until the right OD was obtained).

Steps 4 & 5 were completed for bacteria. When proteins were used, these two steps were ignored.

4. The bacteria was brought to optical density of 2.0 at 600 nm to the absorbance of 0.9-1.0 in PBS (the induced culture was spun down first and then brought up in PBS to OD).
5. A total of 3 ml of bacterial culture was spun down in an ependorff tube. The bacterial pellet was then resuspended in 100 micro liter PBS.
6. 25 micro liter of PBS was placed in every well of a V-bottom microtiter plate.
7. Next, 25 micro liters of appropriate bacteria (or protein) was added in the first well of each row. Typically at least triplicate of the same bacteria was used on the same plate.
8. With a multi-channel pipet a 2-fold serial dilution was done of the bacterial culture (or protein) by completing the following steps:
   a. the bacteria and PBS were mixed in first well.
   b. 25 micro liters were removed and put in the next well;
   c. the contents of the wells were mixed;
   d. steps b and c were repeated for serial dilution.
9. 25 micro liters of the appropriate blood were added to each row (changing tips in between). The wells were taped lightly to evenly distribute the liquid in the wells.
10. The wells were covered and placed in 4 degree Celcius cold room until the plate was read.

The results of this assay are disclosed in Table A.

Example 4

Infection of Bladder Cells in vitro (Adherence Assay)

The infection of bladder cells in vitro was carried out according to the following steps:

Preparation of Tissue Culture Cells (Type 5637 Bladder Cell Line)

1. Place 1 ml of RPMI/10% FBS containing 1:20 dilution of 5637 cells in each well of 24 well plate.
2. Place in incubator for 3 days or until confluent growth.

Preparation of Bacterial Cells (Strains NU14 and UTI89)

1. Inoculate 20 ml of LB containing NU14 with a single colony or a loop from a frozen stock to a 250 ml flask.
2. Static growth at 37° C. for 2 days to induce pili production.
3. Harvest cells at 4,000×g for 10 minutes.
4. Resuspend in 5 ml of PBS (~109 cells/ml)
5. Dilute 1:100 in PBS.

Infection of Tissue Culture Cells In Vitro

1. Wash each well with PBS MgCl$_2$/CaCl$_2$.
2. Place 1 ml of fresh medium to each well.
3. Add 10 μl of bacterial cells to each well. Triplicate plates.
4. Spin plate at 1800 rpm for 5 minutes.
5. View under 40× to see ~2-3 bacterial cells/epithelial cell.
6. Place in lower incubator for 2 hours.
7. Wash two plates 5× with PBS MgCl$_2$/CaCl$_2$. Lyse by addition of 0.1% sarkosyl/0.5% glucose/PBS—MgCl$_2$/CaCl$_2$ one set and dilute for CFU.

The results of this assay are disclosed in Table A.

Example 5

Biofilm Assay

The Biofilm Assay was carried out according to the following steps:

Day 1 Set Up Biofilm Growth on PVC Plates

1. Sterilize PVC plates (96-well round bottom polyvinyl chloride [PVC] plates; Falcon #353911) and PVC Lids (Falcon #353913) in tissue culture hood under UV irradiation for at least 30 min.

2. Make dilution (from overnight cultures) or suspension (from either colonies on plates or freezer stocks) of bacterial cultures. Make enough of bacterial cultures for the number of wells needed. Bacterial culture need to be very dilute: at least 1:1,000 fold dilution from overnight cultures or a small quantity from colonies or freezer stocks.

3. Add 100 μl of bacterial cultures into each well. Make sure to have 1 well with LB alone as negative control and 1 well without anything for blank.

4. Cover plates with lids and leave plates undisturbed at room temperature for 48 hrs.

Day 3 Assay Biofilm With Crystal Violet Stain
Wash Biofilm Plates

5. Prepare enough PBS (w/out $Mg^{2+}$ $Ca^{2+}$) to wash biofilm plates (need at least 3 L PBS for 1-5 plates). Could use $mpH_2O$ instead of PBS.

6. Get a clean 4 L plastic beaker. Cover the bench with a large piece of absorbent pad.

7. Fill 3 containers (large enough to dip the 96-well plates in) with PBS.

8. Start washing a biofilm plate by dumping out bacterial cultures into the beaker. (Treat contents in this beaker as biohazard. Need to bleach the content before emptying it into drain.)

9. Fill the biofilm plate in the first PBS container and shake off PBS in the beaker. Rinse the biofilm 1× in the first PBS container. Put the biofilm plate into the second PBS container and rinse 2×.

10. Put the biofilm plate in the third PBS container and let sit.

11. Proceed to wash a second biofilm plate if there are any.

12. While the second biofilm plate is in the second container, rinse the first biofilm plate 1× and remove it from PBS. Decant residual PBS by banging the plate on paper towels on the bench. Leave the plate up-side-down on a clean paper towel and let the plate dry.

13. Put the second biofilm plate into the third PBS container and let sit.

14. Proceed to wash a third biofilm plate if applicable.

15. Repeat steps 8-14 until all plates are washed.

16. Let washed biofilm plates air-dry for at least 15 min.

Crystal Violet Stain and Wash

17. Fill 4 containers (large enough to dip the 96-well plates in) with PBS.

18. With a multi-channel pipet, add 125 μl of 1% Crystal Violet (in $mpH_2O$). Stain biofilm plates sequentially for 10 min. (not more than 15 min). Give at least 2 minute break in-between staining each plates. If more than 4 biofilm plates, might want to consider staining and washing them in batches.

19. Start washing biofilm plates as above.

20. Let the washed plates air-dry for 10 minor so.

Assay Crystal Violet Stain

21. While plates are drying, prepare EtOH:Acetone (80: 20) solubilization solution. Need 150 μl/well.

Get new flat-bottom 96-well plates (use ELISA plates; Immunon-4).

Set up the Plate Reader.

22. Add 150 μl of solubilization solution into each well to dissolve stained biofilms. Be sure not to splatter to other wells. Change tips if pipet tips become contaminated with crystal violet.

23. After adding solubilization solution to all wells, transfer 100 μl of the dissolved biofilms to a new flat-bottom plate, except the well intended for blank. Change tips in between transfer. Add 100 μl of fresh solubilization solution into the blank well.

24. Proceed immediately to the Plate Reader and read the absorbance of the plate at 600 nm.

25. Continue steps 22-24 for each plate.

The results of this assay are disclosed in Table A.

TABLE A

| | Pilicide Data From Assays | | |
| --- | --- | --- | --- |
| Compound | HA Titer | Adherence Assay % of Wild Type | Bioflim Assay % of Wild Type |
| NU14 | $2^8$ | 100% | 100% |
| | $2^8$ | 97.6% | 73.1% |

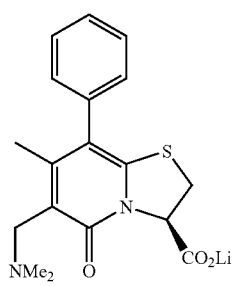

$C_{18}H_{19}LiN_2O_3S$
Exact Mass: 350.1276
Mol. Wt.: 350.3611

TABLE A-continued

Pilicide Data From Assays

| Compound | HA Titer | Adherence Assay % of Wild Type | Bioflim Assay % of Wild Type |
|---|---|---|---|
| $C_{28}H_{25}LiN_2O_3S$<br>Exact Mass: 476.1746<br>Mol. Wt.: 476.5157 | $2^4$ | 21.8% | 6.9% |
| $C_{31}H_{28}LiN_2O_4S$<br>Exact Mass: 531.1930<br>Mol. Wt.: 531.5710 | $2^4$ | 14.3% | 6.8% |
| $C_{27}H_{27}LiN_2O_4S$<br>Exact Mass: 482.1852<br>Mol. Wt.: 482.5203 | $2^3$ | 12.2% | 8.3% |

BIBLIOGRAPHY (1) Li, Q.; Mitscher, L. A.; Shen, L. L. *Medicinal Research Reviews* 2000, 20, 231-293.

(2) Cox, R. J.; O'Hagan, D. *J. Chem. Soc. Perkin Trans. 1* 1991, 2537.

(3) Nagarajan, M.; Xiao, X. S.; Antony, S.; Kohlhagen, G.; Pommier, Y.; Cushman, M. *Journal of Medicinal Chemistry* 2003, 46, 5712-5724.

(4) Hasvold, L. A.; Wang, W. B.; Gwaltney, S. L.; Rockway, T. W.; Nelson, L. T. J.; Mantei, R. A.; Fakhoury, S. A.; Sullivan, G. M.; Li, Q.; Lin, N. H.; Wang, L.; Zhang, H. Y.; Cohen, J.; Gu, W. Z.; Marsh, K.; Bauch, J.; Rosenberg, S.; Sham, F. L. *Bioorganic & Medicinal Chemistry Letters* 2003, 13, 4001-4005.

(5) Thorsett, E. D.; Latimer, L. H. *Curr. Opin. Chem. Biol.* 2000, 4, 377-382.

(6) Emtenas, H.; Alderin, L.; Almqvist, F. *Journal of Organic Chemistry* 2001, 66, 6756-6761.

(7) Emtenas, H.; Ahlin, K.; Pinkner, J. S.; Hultgren, S. J.; Almqvist, F. *Journal of Combinatorial Chemistry* 2002, 4, 630-639.

(8) Mulvey, M. A. *Cellular Microbiology* 2002, 4, 257-271.

(9) Lee, Y. M.; Almqvist, F.; Hultgren, S. J. *Current Opinion in Pharmacology* 2003, 3, 513-519.

(10) Svensson, A.; Larsson, A.; Emtenas, H.; Hedenstrom, M.; Fex, T.; Huitgren, S. J.; Pinkner, J. S.; Almqvist, F.; Kihlberg, J. *Chembiochem* 2001, 2, 915-918.

(11) Emtenas, H.; Taflin, C.; Almqvist, F. *Molecular Diversity* 2003, 7, 165-169.

(12) Rounds, W. D.; Eaton, J. T.; Urbanowicz, J. H.; Gribble, G. W. *Tetrahedron Letters* 1988, 29, 6557-6560.

(13) Butler, R. N. In *Comprehensive Heterocyclic Chemistry;* Katritzky, A. R., Rees, C. W., Eds.; Pergamon Press: Oxford, 1984; Vol. 5, p 791-838.

(14) Lange, U. E. W.; Schafer, B.; Baucke, D.; Buschmann, E.; Mack, H. *Tetrahedron Letters* 1999, 40, 7067-7070.

(15) Graham L, P. *An introduction to medicinal chemistry* 2001, 2, 400-402.

(16) Hanessian, S.; McNaughton-Smith, G.; Lombart, H.-G.; Lubell, W. D. *Tetrahedron* 1997, 53, 12789-12854.

(17) Ellis, G. P.; Romneyalexander, T. M. *Chemical Reviews* 1987, 87, 779-794.

(18) Sundermeier, M.; Zapf, A.; Beller, M. *European Journal of Inorganic Chemistry* 2003, 3513-3526.

(19) Patel, A. K.; Mayadeo, M. S.; Deodhar, K. D. *Indian Journal of Chemistry Section B-Organic Chemistry Including Medicinal Chemistry* 1987, 26, 1099-1101.

(20) Asherson, J. L.; Young D,W, *Journal of the Chemical Society Perkin Trans* 1 1980, 2, 512-528.

(21) Sharifi, A.; Mirzaei, M.; Naimi-Jamal, M. R. *Monatshefte Fur Chemie* 2001, 132, 875-880.

(22) Mojtahedi, M. M.; Sharifi, A.; Mohsenzadeh, F.; Saidi, M. R. *Synthetic Communications* 2000, 30, 69-72.

(23) Padwa, A.; Sheehan, S. M.; Straub, C. S. *Journal of Organic Chemistry* 1999, 64, 8648-8659.

(24) Jin, F. Q.; Confalone, P. N. *Tetrahedron Letters* 2000, 41, 3271-3273.

(25) Alterman, M.; Hallberg, A. *Journal of Organic Chemistry* 2000, 65, 7984-7989.

(26) Arvela, R. K.; Leadbeater, N. E.; Torenius, H. M.; Tye, H. *Organic & Biomolecular Chemistry* 2003, 1, 1119-1121.

(27) Arvela, R. K.; Leadbeater, N. E. *Journal of Organic Chemistry* 2003, 68, 9122-9125.

(28) Leadbeater, N. E.; Torenius, H. M.; Tye, H. *Tetrahedron* 2003, 59, 2253-2258.

(29) Khanapure, S. P.; Saha, G.; Sivendran, S.; Powell, W. S.; Rokach, J. *Tetrahedron Letters* 2000, 41, 5653-5657.

(30) Brana, M. F.; Rodriguez, M. L. *Journal of Heterocyclic chemistry* 1982, 19, 1297-1300.

(31) Clive, D. L. J.; Hisaindee, S. *Journal of Organic Chemistry* 2000, 65, 4923-4929.

(32) Aggarwal, V. K.; Alonso, E.; Hynd, G.; Lydon, K. M.; Palmer, M. J.; Porcelloni, M.; Studley, J. R. *Angewandte Chemie-International Edition* 2001, 40, 1430-+.

(33) Letinois, S.; Dumur, J. C.; Henin, F.; Muzart, J. *Tetrahedron Letters* 1998, 39, 2327-2330.

(34) Brown, H. C.; Kanth, J. V. B.; Zaidlewicz, M. *Tetrahedron* 1999, 55, 5991-6000.

(35) Brown, H. C.; Kanth, J. V. B.; Zaidlewicz, M. *Journal of Organic Chemistry* 1998, 63, 5154-5163.

(36) Cha, J. S.; Brown, H. C. *Journal of Organic Chemistry* 1993, 58, 3974-3979.

(37) Marlett, E. M.; Park, W. S. *Journal of Organic Chemistry* 1990, 55, 2968-2969.

(38) Brown, H. C. *Journal of Organic Chemistry* 1982, 47, 3153-3163.

(39) Mannich, C. K., W. *W. Arch. Pharm* 1912, 250, 647.

(40) Arend, M.; Westermann, B.; Risch, N. *Angew. Chem. Int. Ed* 1998, 37, 1045-1070.

(41) Böhme, H. H., M *Advanced organic chemistry* 1976, 9, 107.

(42) Böhme, H.; Hartke, K. *Chemische Berichte* 1960, 93, 1305-1309.

(43) Heaney, H.; Papageorgiou, G.; Wilkins, R. F. *Tetrahedron* 1997, 53, 2941-2958.

What is claimed is:

1. An amino methylated 2-pyridinone corresponding to the following formula or a salt thereof:

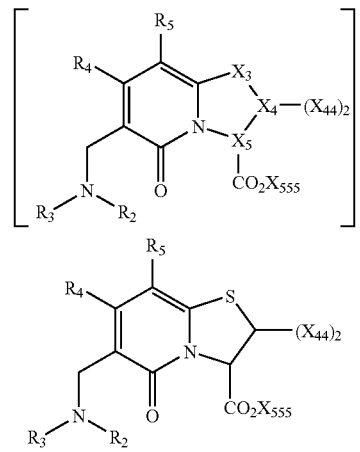

wherein $R_2$ and $R_3$ are independently hydrogen, hydrocarbyl, substituted hydrocarbyl or heterocyclo or, in combination with the nitrogen atom to which they are bonded, form a heterocyclo, provided at least one of $R_2$ and $R_3$ is other than hydrogen;

$R_4$ and $R_5$ are independently hydrogen, hydrocarbyl, substituted hydrocarbyl, or heterocyclo, provided at least one of $R_4$ and $R_5$ is other than hydrogen;

each $X_{44}$ is independently hydrogen or hydrocarbyl; and $X_{555}$ is hydrogen, alkyl or alkali metal cation.

2. The amino methylated 2-pyridinone of claim 1 corresponding to the following formula or a salt thereof:

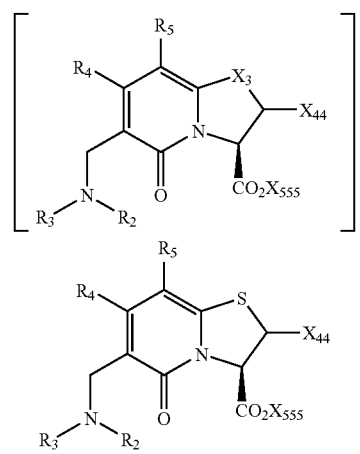

wherein $R_2$ and $R_3$ are independently hydrogen, hydrocarbyl, substituted hydrocarbyl or heterocyclo or, in combination with the nitrogen atom to which they are bonded, form a heterocyclo, provided at least one of $R_2$ and $R_3$ is other than hydrogen;

$R_4$ and $R_5$ are independently hydrogen, hydrocarbyl, substituted hydrocarbyl, or heterocyclo, provided at least one of $R_4$ and $R_5$ is other than hydrogen;
$X_{44}$ is hydrogen or hydrocarbyl; and
$X_{555}$ is hydrogen, alkyl or alkali metal cation.

3. The amino methylated 2-pyridinone of claim 1 corresponding to the following formula or a salt thereof:

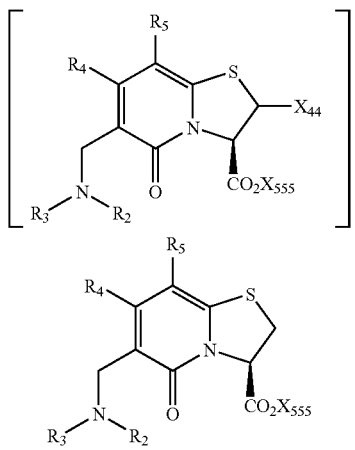

wherein
$R_2$ and $R_3$ are independently hydrogen, hydrocarbyl, substituted hydrocarbyl or heterocyclo or, in combination with the nitrogen atom to which they are bonded, form a heterocyclo, provided at least one of $R_2$ and $R_3$ is other than hydrogen;
$R_4$ and $R_5$ are independently hydrogen, hydrocarbyl, substituted hydrocarbyl, or heterocyclo, provided at least one of $R_4$ and $R_5$ is other than hydrogen; and
$X_{555}$ is hydrogen, alkyl or alkali metal cation.

4. The amino methylated 2-pyridinone of claim 2 wherein $X_{44}$ is hydrogen or alkyl.

5. The amino methylated 2-pyridinone of claim 1 wherein (i) $R_2$ and $R_3$ are independently hydrogen, hydrocarbyl, substituted hydrocarbyl or heterocyclo, provided at least one of $R_2$ and $R_3$ is other than hydrogen.

6. The amino methylated 2-pyridinone of claim 3 wherein $R_2$ and $R_3$ are independently hydrogen or hydrocarbyl.

7. The amino methylated 2-pyridinone of claim 3 wherein $R_2$ is alkyl.

8. The amino methylated 2-pyridinone of claim 2 wherein $R_2$ and $R_3$, in combination with the nitrogen atom to which they are bonded, form a heterocyclo.

9. The amino methylated 2-pyridinone of claim 2 wherein $R_4$ is alkyl or aryl.

10. The amino methylated 2-pyridinone of claim 2 wherein $R_5$ is alkyl.

11. The amino methylated 2-pyridinone of claim 1 wherein each $X_{44}$ is hydrogen.

12. The amino methylated 2-pyridinone of claim 1 wherein each $X_{44}$ is hydrogen and $X_{555}$ is hydrogen or alkyl.

13. The amino methylated 2-pyridinone of claim 1 wherein X555 is hydrogen or methyl.

14. An amino methylated 2-pyridinone corresponding to the following formula or a salt thereof:

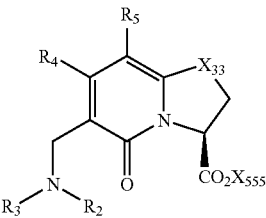

wherein
$R_2$ and $R_3$ are independently hydrogen, hydrocarbyl, substituted hydrocarbyl or heterocyclo or, in combination with the nitrogen atom to which they are bonded, form a heterocyclo, provided at least one of $R_2$ and $R_3$ is other than hydrogen;
$R_4$ and $R_5$ are independently hydrogen, hydrocarbyl, substituted hydrocarbyl, or heterocyclo, provided at least one of $R_4$ and $R_5$ is other than hydrogen;
$X_{33}$ is sulfur; and
$X_{555}$ is hydrogen or alkali metal cation.

15. The amino methylated 2-pyridinone of claim 14 wherein $R_2$ and $R_3$ are independently hydrogen, hydrocarbyl, substituted hydrocarbyl or heterocyclo, provided at least one of $R_2$ and $R_3$ is other than hydrogen.

16. The amino methylated 2-pyridinone of claim 14 wherein $R_2$ is alkyl.

17. The amino methylated 2-pyridinone of claim 14 wherein $R_2$ and $R_3$, in combination with the nitrogen atom to which they are bonded, form a heterocyclo.

18. The amino methylated 2-pyridinone of claim 14 wherein $R_4$ is alkyl or aryl.

19. The amino methylated 2-pyridinone of claim 14 wherein $R_5$ is alkyl.

20. The amino methylated 2-pyridinone of claim 14 wherein $X_{555}$ is hydrogen.

21. A compound having the formula

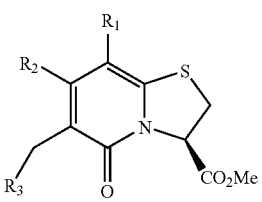

wherein $R_1$, $R_2$, and $R_3$, in combination, are selected from the combinations identified in the following table as combinations 8a-8f:

| Combination No. | $R^1$ | $R^2$ | $R^3$ |
| --- | --- | --- | --- |
| 8a | phenyl | methyl | NMe₂ |
| 8b | phenyl | methyl | morpholine |
| 8c | phenyl | CH₂-1-naphtyl | NMe₂ |
| 8d | phenyl | CH₂-1-naphtyl | morpholine |
| 8e | cyclopropyl | CH₂-1-naphtyl | NMe₂ |
| 8f | cyclopropyl | CH₂-1-naphtyl | morpholine. |

* * * * *